(12) United States Patent
Nicholas et al.

(10) Patent No.: US 12,053,180 B2
(45) Date of Patent: *Aug. 6, 2024

(54) HANDHELD SURGICAL HANDLE ASSEMBLY, SURGICAL ADAPTERS FOR USE BETWEEN SURGICAL HANDLE ASSEMBLY AND SURGICAL END EFFECTORS, AND METHODS OF USE

(71) Applicant: Covidien LP, Mansfield, MA (US)

(72) Inventors: David Nicholas, Trumbull, CT (US);
Russell Pribanic, Roxbury, CT (US);
John Beardsley, Wallingford, CT (US);
Michael Zemlok, Prospect, CT (US)

(73) Assignee: Covidien LP, Mansfield, MA (US)

( * ) Notice: Subject to any disclaimer, the term of this patent is extended or adjusted under 35 U.S.C. 154(b) by 449 days.

This patent is subject to a terminal disclaimer.

(21) Appl. No.: 17/386,156

(22) Filed: Jul. 27, 2021

(65) Prior Publication Data

US 2022/0022870 A1 Jan. 27, 2022

Related U.S. Application Data

(63) Continuation of application No. 16/773,798, filed on Jan. 27, 2020, now Pat. No. 11,071,546, which is a
(Continued)

(51) Int. Cl.
*A61B 17/068* (2006.01)
*A61B 17/00* (2006.01)
(Continued)

(52) U.S. Cl.
CPC ...... *A61B 17/07207* (2013.01); *A61B 17/068* (2013.01); *A61B 17/32* (2013.01);
(Continued)

(58) Field of Classification Search
CPC ... A61B 17/07207; A61B 17/32; A61B 17/34; A61B 17/68; A61B 17/1155; A61B 19/2203
See application file for complete search history.

(56) References Cited

U.S. PATENT DOCUMENTS 2,777,340 A 1/1957 Hettwer et al.
2,957,353 A 10/1960 Babacz
(Continued)

FOREIGN PATENT DOCUMENTS

AU 2008229795 A1 4/2009
CA 2451558 A1 1/2003
(Continued)

OTHER PUBLICATIONS

International Search Report corresponding to PCT/US2005/027266, completed May 30, 2008 and mailed Jun. 18, 2008; (2 pp.).
(Continued)

*Primary Examiner* — Timothy J Neal
*Assistant Examiner* — William B Chou
(74) *Attorney, Agent, or Firm* — Carter, DeLuca & Farrell LLP

(57) ABSTRACT

The present disclosure relates to a surgical device including an adapter assembly for selectively interconnecting an end effector and the device housing. The adapter assembly includes at least one drive converter assembly that converts and transmits a rotation of the rotatable drive shaft to an axial translation of at least one axially translatable drive member of the end effector. A first drive converter assembly includes a first drive element, a nut, an articulation sleeve, an articulation bearing, and an articulation link. Rotation of the rotatable drive shaft results in rotation of the first drive element. Rotation of the first drive element results in axial translation of the nut, the articulation sleeve, the articulation
(Continued)

bearing, the articulation link, and the at least one axially translatable drive member of the end effector.

12 Claims, 20 Drawing Sheets

Related U.S. Application Data continuation of application No. 15/451,472, filed on Mar. 7, 2017, now Pat. No. 10,542,984, which is a continuation of application No. 13/875,571, filed on May 2, 2013, now Pat. No. 9,597,104.

(60) Provisional application No. 61/654,191, filed on Jun. 1, 2012.

(51) Int. Cl.
    *A61B 17/072*     (2006.01)
    *A61B 17/29*     (2006.01)
    *A61B 17/32*     (2006.01)
    *A61B 90/90*     (2016.01)
    *F16H 25/20*     (2006.01)

(52) U.S. Cl.
CPC .............. *A61B 90/90* (2016.02); *F16H 25/20* (2013.01); *A61B 2017/00017* (2013.01); *A61B 2017/00398* (2013.01); *A61B 2017/0046* (2013.01); *A61B 2017/00473* (2013.01); *A61B 2017/00477* (2013.01); *A61B 2017/00526* (2013.01); *A61B 2017/00734* (2013.01); *A61B 2017/00831* (2013.01); *A61B 2017/00902* (2013.01); *A61B 2017/07285* (2013.01); *A61B 2017/2929* (2013.01); *A61B 2017/2948* (2013.01); *A61B 2560/0214* (2013.01); *F16H 2025/2043* (2013.01)

(56) References Cited

U.S. PATENT DOCUMENTS

| | | |
|---|---|---|
| 3,111,328 A | 11/1963 | Di Rito et al. |
| 3,695,058 A | 10/1972 | Keith, Jr. |
| 3,734,515 A | 5/1973 | Dudek |
| 3,759,336 A | 9/1973 | Marcovitz et al. |
| 4,162,399 A | 7/1979 | Hudson |
| 4,606,343 A | 8/1986 | Conta et al. |
| 4,705,038 A | 11/1987 | Sjostrom et al. |
| 4,722,685 A | 2/1988 | de Estrada et al. |
| 4,823,807 A | 4/1989 | Russell et al. |
| 4,874,181 A | 10/1989 | Hsu |
| 5,129,118 A | 7/1992 | Walmesley |
| 5,129,570 A | 7/1992 | Schulze et al. |
| 5,152,744 A | 10/1992 | Krause et al. |
| 5,301,061 A | 4/1994 | Nakada et al. |
| 5,312,023 A | 5/1994 | Green et al. |
| 5,326,013 A | 7/1994 | Green et al. |
| 5,350,355 A | 9/1994 | Sklar |
| 5,383,874 A | 1/1995 | Jackson et al. |
| 5,383,880 A | 1/1995 | Hooven |
| 5,389,098 A | 2/1995 | Tsuruta et al. |
| 5,395,033 A | 3/1995 | Byrne et al. |
| 5,400,267 A | 3/1995 | Denen et al. |
| 5,411,508 A | 5/1995 | Bessler et al. |
| 5,413,267 A | 5/1995 | Solyntjes et al. |
| 5,427,087 A | 6/1995 | Ito et al. |
| 5,467,911 A | 11/1995 | Tsuruta et al. |
| 5,476,379 A | 12/1995 | Disel |
| 5,487,499 A | 1/1996 | Sorrentino et al. |
| 5,518,163 A | 5/1996 | Hooven |
| 5,518,164 A | 5/1996 | Hooven |
| 5,526,822 A | 6/1996 | Burbank et al. |
| 5,529,235 A | 6/1996 | Boiarski et al. |
| 5,535,934 A | 7/1996 | Boiarski et al. |
| 5,535,937 A | 7/1996 | Boiarski et al. |
| 5,540,375 A | 7/1996 | Bolanos et al. |
| 5,540,706 A | 7/1996 | Aust et al. |
| 5,542,594 A | 8/1996 | McKean et al. |
| 5,549,637 A | 8/1996 | Crainich |
| 5,553,675 A | 9/1996 | Pitzen et al. |
| 5,562,239 A | 10/1996 | Boiarski et al. |
| 5,564,615 A | 10/1996 | Bishop et al. |
| 5,609,560 A | 3/1997 | Ichikawa et al. |
| 5,632,432 A | 5/1997 | Schulze et al. |
| 5,653,374 A | 8/1997 | Young et al. |
| 5,658,300 A | 8/1997 | Bito et al. |
| 5,667,517 A | 9/1997 | Hooven |
| 5,693,042 A | 12/1997 | Boiarski et al. |
| 5,704,534 A | 1/1998 | Huitema et al. |
| 5,713,505 A | 2/1998 | Huitema |
| 5,762,603 A | 6/1998 | Thompson |
| 5,779,130 A | 7/1998 | Alesi et al. |
| 5,782,396 A | 7/1998 | Mastri et al. |
| 5,782,397 A | 7/1998 | Koukline |
| 5,820,009 A | 10/1998 | Melling et al. |
| 5,863,159 A | 1/1999 | Lasko |
| 5,865,361 A | 2/1999 | Milliman et al. |
| 5,908,427 A | 6/1999 | McKean et al. |
| 5,954,259 A | 9/1999 | Viola et al. |
| 5,964,774 A | 10/1999 | McKean et al. |
| 5,993,454 A | 11/1999 | Longo |
| 6,010,054 A | 1/2000 | Johnson et al. |
| 6,017,354 A | 1/2000 | Culp et al. |
| 6,032,849 A | 3/2000 | Mastri et al. |
| 6,045,560 A | 4/2000 | McKean et al. |
| 6,090,123 A | 7/2000 | Culp et al. |
| 6,126,651 A | 10/2000 | Mayer |
| 6,129,547 A | 10/2000 | Cise et al. |
| 6,165,169 A | 12/2000 | Panescu et al. |
| 6,171,316 B1 | 1/2001 | Kovac et al. |
| 6,239,732 B1 | 5/2001 | Cusey |
| 6,241,139 B1 | 6/2001 | Milliman et al. |
| 6,264,086 B1 | 7/2001 | McGuckin, Jr. |
| 6,264,087 B1 | 7/2001 | Whitman |
| 6,302,311 B1 | 10/2001 | Adams et al. |
| 6,315,184 B1 | 11/2001 | Whitman |
| 6,321,855 B1 | 11/2001 | Barnes |
| 6,329,778 B1 | 12/2001 | Culp et al. |
| 6,343,731 B1 | 2/2002 | Adams et al. |
| 6,348,061 B1 | 2/2002 | Whitman |
| 6,368,324 B1 | 4/2002 | Dinger et al. |
| 6,371,909 B1 | 4/2002 | Hoeg et al. |
| 6,434,507 B1 | 8/2002 | Clayton et al. |
| 6,443,973 B1 | 9/2002 | Whitman |
| 6,461,372 B1 | 10/2002 | Jensen et al. |
| 6,488,197 B1 | 12/2002 | Whitman |
| 6,491,201 B1 | 12/2002 | Whitman |
| 6,533,157 B1 | 3/2003 | Whitman |
| 6,537,280 B2 | 3/2003 | Dinger et al. |
| 6,610,066 B2 | 8/2003 | Dinger et al. |
| 6,611,793 B1 | 8/2003 | Burnside et al. |
| 6,645,218 B1 | 11/2003 | Cassidy et al. |
| 6,654,999 B2 | 12/2003 | Stoddard et al. |
| 6,698,643 B2 | 3/2004 | Whitman |
| 6,699,177 B1 | 3/2004 | Wang et al. |
| 6,716,233 B1 | 4/2004 | Whitman |
| 6,743,240 B2 | 6/2004 | Smith et al. |
| 6,783,533 B2 | 8/2004 | Green et al. |
| 6,792,390 B1 | 9/2004 | Burnside et al. |
| 6,793,652 B1 | 9/2004 | Whitman et al. |
| 6,817,508 B1 | 11/2004 | Racenet et al. |
| 6,830,174 B2 | 12/2004 | Hillstead et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| 6,905,057 B2 | 6/2005 | Swayze et al. |
| 6,959,852 B2 | 11/2005 | Shelton, IV et al. |
| 6,964,363 B2 | 11/2005 | Wales et al. |
| 6,981,628 B2 | 1/2006 | Wales |
| 6,981,941 B2 | 1/2006 | Whitman et al. |
| 6,986,451 B1 | 1/2006 | Mastri et al. |
| 6,988,649 B2 | 1/2006 | Shelton, IV et al. |
| 7,032,798 B2 | 4/2006 | Whitman et al. |

(56) References Cited

U.S. PATENT DOCUMENTS

| | | |
|---|---|---|
| RE39,152 E | 6/2006 | Aust et al. |
| 7,055,731 B2 | 6/2006 | Shelton, IV et al. |
| 7,059,508 B2 | 6/2006 | Shelton, IV et al. |
| 7,077,856 B2 | 7/2006 | Whitman |
| 7,111,769 B2 | 9/2006 | Wales et al. |
| 7,122,029 B2 | 10/2006 | Koop et al. |
| 7,140,528 B2 | 11/2006 | Shelton, IV |
| 7,143,923 B2 | 12/2006 | Shelton, IV et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,172,104 B2 | 2/2007 | Scirica et al. |
| 7,225,964 B2 | 6/2007 | Mastri et al. |
| 7,238,021 B1 | 7/2007 | Johnson |
| 7,246,734 B2 | 7/2007 | Shelton, IV |
| 7,328,828 B2 | 2/2008 | Ortiz et al. |
| 7,364,061 B2 | 4/2008 | Swayze et al. |
| 7,380,695 B2 | 6/2008 | Doll et al. |
| 7,380,696 B2 | 6/2008 | Shelton, IV et al. |
| 7,404,508 B2 | 7/2008 | Smith et al. |
| 7,407,078 B2 | 8/2008 | Shelton, IV et al. |
| 7,416,101 B2 | 8/2008 | Shelton, IV et al. |
| 7,419,080 B2 | 9/2008 | Smith et al. |
| 7,422,139 B2 | 9/2008 | Shelton, IV et al. |
| 7,431,189 B2 | 10/2008 | Shelton, IV et al. |
| 7,441,684 B2 | 10/2008 | Shelton, IV et al. |
| 7,448,525 B2 | 11/2008 | Shelton, IV et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,481,347 B2 | 1/2009 | Roy |
| 7,481,824 B2 | 1/2009 | Boudreaux et al. |
| 7,487,899 B2 | 2/2009 | Shelton, IV et al. |
| 7,549,564 B2 | 6/2009 | Boudreaux |
| 7,565,993 B2 | 7/2009 | Milliman et al. |
| 7,568,603 B2 | 8/2009 | Shelton, IV et al. |
| 7,575,144 B2 | 8/2009 | Ortiz et al. |
| 7,588,175 B2 | 9/2009 | Timm et al. |
| 7,588,176 B2 | 9/2009 | Timm et al. |
| 7,637,409 B2 | 12/2009 | Marczyk |
| 7,641,093 B2 | 1/2010 | Doll et al. |
| 7,644,848 B2 | 1/2010 | Swayze et al. |
| 7,670,334 B2 | 3/2010 | Hueil et al. |
| 7,673,780 B2 | 3/2010 | Shelton, IV et al. |
| 7,699,835 B2 | 4/2010 | Lee et al. |
| 7,721,931 B2 | 5/2010 | Shelton, IV et al. |
| 7,738,971 B2 | 6/2010 | Swayze et al. |
| 7,740,159 B2 | 6/2010 | Shelton, IV et al. |
| 7,743,960 B2 | 6/2010 | Whitman et al. |
| 7,758,613 B2 | 7/2010 | Whitman |
| 7,766,210 B2 | 8/2010 | Shelton, IV et al. |
| 7,770,773 B2 | 8/2010 | Whitman et al. |
| 7,770,775 B2 | 8/2010 | Shelton, IV et al. |
| 7,793,812 B2 | 9/2010 | Moore et al. |
| 7,799,039 B2 | 9/2010 | Shelton, IV et al. |
| 7,802,712 B2 | 9/2010 | Milliman et al. |
| 7,803,151 B2 | 9/2010 | Whitman |
| 7,819,896 B2 | 10/2010 | Racenet |
| 7,822,458 B2 | 10/2010 | Webster, III et al. |
| 7,845,534 B2 | 12/2010 | Viola et al. |
| 7,845,537 B2 | 12/2010 | Shelton, IV et al. |
| 7,857,185 B2 | 12/2010 | Swayze et al. |
| 7,870,989 B2 | 1/2011 | Viola et al. |
| 7,905,897 B2 | 3/2011 | Whitman et al. |
| 7,918,230 B2 | 4/2011 | Whitman et al. |
| 7,922,061 B2 | 4/2011 | Shelton, IV et al. |
| 7,922,719 B2 | 4/2011 | Ralph et al. |
| 7,947,034 B2 | 5/2011 | Whitman |
| 7,951,071 B2 | 5/2011 | Whitman et al. |
| 7,954,682 B2 | 6/2011 | Giordano et al. |
| 7,959,051 B2 | 6/2011 | Smith et al. |
| 7,963,433 B2 | 6/2011 | Whitman et al. |
| 7,967,178 B2 | 6/2011 | Scirica et al. |
| 7,967,179 B2 | 6/2011 | Olson et al. |
| 7,992,758 B2 | 8/2011 | Whitman et al. |
| 8,016,178 B2 | 9/2011 | Olson et al. |
| 8,016,855 B2 | 9/2011 | Whitman et al. |
| 8,020,743 B2 | 9/2011 | Shelton, IV |
| 8,025,199 B2 | 9/2011 | Whitman et al. |
| 8,035,487 B2 | 10/2011 | Malackowski |
| 8,052,024 B2 | 11/2011 | Viola et al. |
| 8,056,787 B2 | 11/2011 | Boudreaux et al. |
| 8,114,118 B2 | 2/2012 | Knodel et al. |
| 8,132,705 B2 | 3/2012 | Viola et al. |
| 8,152,516 B2 | 4/2012 | Harvey et al. |
| 8,157,150 B2 | 4/2012 | Viola et al. |
| 8,157,151 B2 | 4/2012 | Ingmanson et al. |
| 8,182,494 B1 | 5/2012 | Yencho et al. |
| 8,186,555 B2 | 5/2012 | Shelton, IV et al. |
| 8,186,587 B2 | 5/2012 | Zmood et al. |
| 8,220,367 B2 | 7/2012 | Hsu |
| 8,235,273 B2 | 8/2012 | Olson et al. |
| 8,241,322 B2 | 8/2012 | Whitman et al. |
| 8,272,554 B2 | 9/2012 | Whitman et al. |
| 8,292,150 B2 | 10/2012 | Bryant |
| 8,292,888 B2 | 10/2012 | Whitman |
| 8,303,581 B2 | 11/2012 | Arts et al. |
| 8,342,379 B2 | 1/2013 | Whitman et al. |
| 8,348,855 B2 | 1/2013 | Hillely et al. |
| 8,353,440 B2 | 1/2013 | Whitman et al. |
| 8,357,144 B2 | 1/2013 | Whitman et al. |
| 8,365,633 B2 | 2/2013 | Simaan et al. |
| 8,365,972 B2 | 2/2013 | Aranyi et al. |
| 8,371,492 B2 | 2/2013 | Aranyi et al. |
| 8,372,057 B2 | 2/2013 | Cude et al. |
| 8,391,957 B2 | 3/2013 | Carlson et al. |
| 8,424,739 B2 | 4/2013 | Racenet et al. |
| 8,454,585 B2 | 6/2013 | Whitman |
| 8,505,802 B2 | 8/2013 | Viola et al. |
| 8,517,241 B2 | 8/2013 | Nicholas et al. |
| 8,551,076 B2 | 10/2013 | Duval et al. |
| 8,561,871 B2 | 10/2013 | Rajappa et al. |
| 8,623,000 B2 | 1/2014 | Humayun et al. |
| 8,632,463 B2 | 1/2014 | Drinan et al. |
| 8,647,258 B2 | 2/2014 | Aranyi et al. |
| 8,657,174 B2 | 2/2014 | Yates et al. |
| 8,657,177 B2 | 2/2014 | Scirica et al. |
| 8,672,206 B2 | 3/2014 | Aranyi et al. |
| 8,696,552 B2 | 4/2014 | Whitman |
| 8,708,213 B2 | 4/2014 | Shelton, IV et al. |
| 8,752,749 B2 | 6/2014 | Moore et al. |
| 8,758,391 B2 | 6/2014 | Swayze et al. |
| 8,806,973 B2 | 8/2014 | Ross et al. |
| 8,851,355 B2 | 10/2014 | Aranyi et al. |
| 8,858,571 B2 | 10/2014 | Shelton, IV et al. |
| 8,875,972 B2 | 11/2014 | Weisenburgh, II et al. |
| 8,893,946 B2 | 11/2014 | Boudreaux et al. |
| 8,899,462 B2 | 12/2014 | Kostrzewski et al. |
| 8,939,344 B2 | 1/2015 | Olson et al. |
| 8,960,519 B2 | 2/2015 | Whitman et al. |
| 8,961,396 B2 | 2/2015 | Azarbarzin et al. |
| 8,967,443 B2 | 3/2015 | McCuen |
| 8,968,276 B2 | 3/2015 | Zemlok et al. |
| 8,968,337 B2 | 3/2015 | Whitfield et al. |
| 8,992,422 B2 | 3/2015 | Spivey et al. |
| 9,064,653 B2 | 6/2015 | Prest et al. |
| 9,113,875 B2 | 8/2015 | Viola et al. |
| 9,216,013 B2 | 12/2015 | Scirica et al. |
| 9,282,961 B2 | 3/2016 | Whitman et al. |
| 9,282,963 B2 | 3/2016 | Bryant |
| 9,295,522 B2 | 3/2016 | Kostrzewski |
| 9,307,986 B2 | 4/2016 | Hall et al. |
| 9,597,104 B2 | 3/2017 | Nicholas et al. |
| 2002/0049454 A1 | 4/2002 | Whitman et al. |
| 2002/0165541 A1 | 11/2002 | Whitman |
| 2003/0038938 A1 | 2/2003 | Jung et al. |
| 2003/0165794 A1 | 9/2003 | Matoba |
| 2004/0111012 A1 | 6/2004 | Whitman |
| 2004/0133189 A1 | 7/2004 | Sakurai |
| 2004/0176751 A1 | 9/2004 | Weitzner et al. |
| 2005/0103819 A1 | 5/2005 | Racenet et al. |
| 2005/0131442 A1 | 6/2005 | Yachia et al. |
| 2006/0142656 A1 | 6/2006 | Malackowski et al. |
| 2006/0142740 A1 | 6/2006 | Sherman et al. |

(56) References Cited

U.S. PATENT DOCUMENTS

| | | |
|---|---|---|
| 2006/0278680 A1 | 12/2006 | Viola et al. |
| 2007/0023476 A1 | 2/2007 | Whitman et al. |
| 2007/0023477 A1 | 2/2007 | Whitman et al. |
| 2007/0029363 A1 | 2/2007 | Popov |
| 2007/0055219 A1 | 3/2007 | Whitman et al. |
| 2007/0084897 A1 | 4/2007 | Shelton et al. |
| 2007/0102472 A1 | 5/2007 | Shelton |
| 2007/0152014 A1 | 7/2007 | Gillum et al. |
| 2007/0175949 A1 | 8/2007 | Shelton et al. |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0175961 A1 | 8/2007 | Shelton et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0058801 A1 | 3/2008 | Taylor et al. |
| 2008/0109012 A1 | 5/2008 | Falco et al. |
| 2008/0110958 A1 | 5/2008 | McKenna et al. |
| 2008/0167736 A1 | 7/2008 | Swayze et al. |
| 2008/0185419 A1 | 8/2008 | Smith et al. |
| 2008/0188841 A1 | 8/2008 | Tomasello et al. |
| 2008/0197167 A1 | 8/2008 | Viola et al. |
| 2008/0208195 A1 | 8/2008 | Shores et al. |
| 2008/0237296 A1 | 10/2008 | Boudreaux et al. |
| 2008/0249551 A1 | 10/2008 | Sunaoshi et al. |
| 2008/0251561 A1 | 10/2008 | Eades et al. |
| 2008/0255413 A1 | 10/2008 | Zemlok et al. |
| 2008/0255607 A1 | 10/2008 | Zemlok |
| 2008/0262654 A1 | 10/2008 | Omori et al. |
| 2008/0308603 A1 | 12/2008 | Shelton et al. |
| 2009/0090763 A1 | 4/2009 | Zemlok et al. |
| 2009/0099876 A1 | 4/2009 | Whitman |
| 2009/0138006 A1 | 5/2009 | Bales et al. |
| 2009/0171147 A1 | 7/2009 | Lee et al. |
| 2009/0182193 A1 | 7/2009 | Whitman et al. |
| 2009/0209990 A1 | 8/2009 | Yates et al. |
| 2009/0254094 A1 | 10/2009 | Knapp et al. |
| 2010/0069942 A1 | 3/2010 | Shelton, IV |
| 2010/0193568 A1 | 8/2010 | Scheib et al. |
| 2010/0211053 A1 | 8/2010 | Ross et al. |
| 2010/0225073 A1 | 9/2010 | Porter et al. |
| 2011/0006101 A1 | 1/2011 | Hall et al. |
| 2011/0017801 A1 | 1/2011 | Zemlok et al. |
| 2011/0071508 A1 | 3/2011 | Duval et al. |
| 2011/0077673 A1 | 3/2011 | Grubac et al. |
| 2011/0121049 A1 | 5/2011 | Malinouskas et al. |
| 2011/0125138 A1 | 5/2011 | Malinouskas et al. |
| 2011/0139851 A1 | 6/2011 | McCuen |
| 2011/0155783 A1 | 6/2011 | Rajappa et al. |
| 2011/0155786 A1 | 6/2011 | Shelton, IV |
| 2011/0172648 A1 | 7/2011 | Jeong |
| 2011/0174099 A1 | 7/2011 | Ross et al. |
| 2011/0204119 A1 | 8/2011 | McCuen |
| 2011/0218522 A1 | 9/2011 | Whitman |
| 2011/0253765 A1 | 10/2011 | Nicholas et al. |
| 2011/0276057 A1 | 11/2011 | Conlon et al. |
| 2011/0290854 A1 | 12/2011 | Timm et al. |
| 2011/0295242 A1 | 12/2011 | Spivey et al. |
| 2011/0295269 A1 | 12/2011 | Swensgard et al. |
| 2012/0000962 A1 | 1/2012 | Racenet et al. |
| 2012/0074199 A1 | 3/2012 | Olson et al. |
| 2012/0089131 A1 | 4/2012 | Zemlok et al. |
| 2012/0104071 A1 | 5/2012 | Bryant |
| 2012/0116368 A1 | 5/2012 | Viola |
| 2012/0143002 A1 | 6/2012 | Aranyi et al. |
| 2012/0172924 A1 | 7/2012 | Allen, IV |
| 2012/0223121 A1 | 9/2012 | Viola et al. |
| 2012/0245428 A1 | 9/2012 | Smith et al. |
| 2012/0253329 A1 | 10/2012 | Zemlok et al. |
| 2012/0310220 A1 | 12/2012 | Malkowski et al. |
| 2012/0323226 A1 | 12/2012 | Chowaniec et al. |
| 2012/0330285 A1 | 12/2012 | Hartoumbekis et al. |
| 2013/0018361 A1 | 1/2013 | Bryant |
| 2013/0093149 A1 | 4/2013 | Saur et al. |
| 2013/0098966 A1 | 4/2013 | Kostrzewski et al. |
| 2013/0098968 A1 | 4/2013 | Aranyi et al. |
| 2013/0098969 A1 | 4/2013 | Scirica et al. |
| 2013/0181035 A1 | 7/2013 | Milliman |
| 2013/0184704 A1 | 7/2013 | Beardsley et al. |
| 2013/0214025 A1 | 8/2013 | Zemlok et al. |
| 2013/0240596 A1 | 9/2013 | Whitman |
| 2013/0274722 A1 | 10/2013 | Kostrzewski et al. |
| 2013/0282052 A1 | 10/2013 | Aranyi et al. |
| 2013/0292451 A1 | 11/2013 | Viola et al. |
| 2013/0313304 A1 | 11/2013 | Shelton, IV et al. |
| 2013/0317486 A1 | 11/2013 | Nicholas et al. |
| 2013/0319706 A1 | 12/2013 | Nicholas et al. |
| 2013/0324978 A1 | 12/2013 | Nicholas et al. |
| 2013/0324979 A1 | 12/2013 | Nicholas et al. |
| 2013/0334281 A1 | 12/2013 | Williams |
| 2014/0012236 A1 | 1/2014 | Williams et al. |
| 2014/0012237 A1 | 1/2014 | Pribanic et al. |
| 2014/0012289 A1 | 1/2014 | Snow et al. |
| 2014/0025046 A1 | 1/2014 | Williams et al. |
| 2014/0110455 A1 | 4/2014 | Ingmanson et al. |
| 2014/0207125 A1 | 7/2014 | Applegate et al. |
| 2014/0207182 A1 | 7/2014 | Zergiebel et al. |
| 2014/0236173 A1 | 8/2014 | Scirica et al. |
| 2014/0236174 A1 | 8/2014 | Williams et al. |
| 2014/0276932 A1 | 9/2014 | Williams et al. |
| 2014/0299647 A1 | 10/2014 | Scirica et al. |
| 2014/0303668 A1 | 10/2014 | Nicholas et al. |
| 2014/0358129 A1 | 12/2014 | Zergiebel et al. |
| 2014/0361068 A1 | 12/2014 | Aranyi et al. |
| 2014/0373652 A1 | 12/2014 | Zergiebel et al. |
| 2015/0048144 A1 | 2/2015 | Whitman |
| 2015/0076205 A1 | 3/2015 | Zergiebel |
| 2015/0080912 A1 | 3/2015 | Sapre |
| 2015/0157321 A1 | 6/2015 | Zergiebel et al. |
| 2015/0164502 A1 | 6/2015 | Richard et al. |
| 2015/0272577 A1 | 10/2015 | Zemlok et al. |
| 2015/0297199 A1 | 10/2015 | Nicholas et al. |
| 2015/0303996 A1 | 10/2015 | Calderoni |
| 2015/0320420 A1 | 11/2015 | Penna et al. |
| 2015/0327850 A1 | 11/2015 | Kostrzewski |
| 2015/0342601 A1 | 12/2015 | Williams et al. |
| 2015/0342603 A1 | 12/2015 | Zergiebel et al. |
| 2015/0374366 A1 | 12/2015 | Zergiebel et al. |
| 2015/0374370 A1 | 12/2015 | Zergiebel et al. |
| 2015/0374371 A1 | 12/2015 | Richard et al. |
| 2015/0374372 A1 | 12/2015 | Zergiebel et al. |
| 2015/0374449 A1 | 12/2015 | Chowaniec et al. |
| 2015/0380187 A1 | 12/2015 | Zergiebel et al. |
| 2016/0095585 A1 | 4/2016 | Zergiebel et al. |
| 2016/0095596 A1 | 4/2016 | Scirica et al. |
| 2016/0106406 A1 | 4/2016 | Cabrera et al. |
| 2016/0113648 A1 | 4/2016 | Zergiebel et al. |
| 2016/0113649 A1 | 4/2016 | Zergiebel et al. |

FOREIGN PATENT DOCUMENTS

| | | |
|---|---|---|
| CN | 101856251 A | 10/2010 |
| CN | 101953793 A | 1/2011 |
| CN | 102247182 A | 11/2011 |
| DE | 102008053842 A1 | 5/2010 |
| EP | 0634144 A1 | 1/1995 |
| EP | 0648476 A1 | 4/1995 |
| EP | 0686374 A2 | 12/1995 |
| EP | 0705571 A1 | 4/1996 |
| EP | 1690502 A1 | 8/2006 |
| EP | 1723913 A1 | 11/2006 |
| EP | 1736112 A1 | 12/2006 |
| EP | 1759652 A2 | 3/2007 |
| EP | 1769754 A1 | 4/2007 |
| EP | 1772105 A1 | 4/2007 |
| EP | 1813199 A1 | 8/2007 |
| EP | 1813203 A2 | 8/2007 |
| EP | 1813211 A2 | 8/2007 |
| EP | 1908412 A2 | 4/2008 |
| EP | 1917929 A1 | 5/2008 |
| EP | 1943954 A2 | 7/2008 |
| EP | 1943956 A2 | 7/2008 |

(56) References Cited

FOREIGN PATENT DOCUMENTS

| | | | |
|---|---|---|---|
| EP | 1943958 | A1 | 7/2008 |
| EP | 1943976 | A2 | 7/2008 |
| EP | 1952769 | A2 | 8/2008 |
| EP | 2005898 | A2 | 12/2008 |
| EP | 2027819 | A1 | 2/2009 |
| EP | 2044890 | A1 | 4/2009 |
| EP | 2055243 | A2 | 5/2009 |
| EP | 2090247 | A1 | 8/2009 |
| EP | 2098170 | A2 | 9/2009 |
| EP | 2100561 | A2 | 9/2009 |
| EP | 2100562 | A2 | 9/2009 |
| EP | 2165664 | A2 | 3/2010 |
| EP | 2236098 | A2 | 10/2010 |
| EP | 2245994 | A1 | 11/2010 |
| EP | 2263568 | A2 | 12/2010 |
| EP | 2272443 | A1 | 1/2011 |
| EP | 2316345 | A1 | 5/2011 |
| EP | 2324776 | A2 | 5/2011 |
| EP | 2329773 | A1 | 6/2011 |
| EP | 2333509 | A1 | 6/2011 |
| EP | 2377471 | A1 | 10/2011 |
| EP | 2377472 | A1 | 10/2011 |
| EP | 2446834 | A1 | 5/2012 |
| EP | 2462878 | A1 | 6/2012 |
| EP | 2462880 | B1 | 6/2012 |
| EP | 2491872 | A1 | 8/2012 |
| EP | 2586382 | A2 | 5/2013 |
| EP | 2606834 | A2 | 6/2013 |
| EP | 2668910 | A2 | 12/2013 |
| EP | 2676615 | A2 | 12/2013 |
| EP | 2815705 | A1 | 12/2014 |
| ES | 2333509 | A1 | 2/2010 |
| FR | 2861574 | A1 | 5/2005 |
| JP | 08038488 | | 2/1996 |
| JP | 2005125075 | A | 5/2005 |
| JP | 2011115594 | A | 6/2011 |
| JP | 2011125721 | A | 6/2011 |
| JP | 2011189136 | A | 9/2011 |
| KR | 20120022521 | A | 3/2012 |
| WO | 9915086 | A1 | 4/1999 |
| WO | 0072760 | A1 | 12/2000 |
| WO | 0072765 | A1 | 12/2000 |
| WO | 03000138 | A2 | 1/2003 |
| WO | 03007769 | A2 | 1/2003 |
| WO | 03026511 | A1 | 4/2003 |
| WO | 03030743 | A2 | 4/2003 |
| WO | 03065916 | A1 | 8/2003 |
| WO | 03077769 | A1 | 9/2003 |
| WO | 03090630 | A2 | 11/2003 |
| WO | 2004107989 | A1 | 12/2004 |
| WO | 2006042210 | A2 | 4/2006 |
| WO | 2007016290 | A2 | 2/2007 |
| WO | 2007/026354 | A1 | 3/2007 |
| WO | 2007026354 | A1 | 3/2007 |
| WO | 2007137304 | A2 | 11/2007 |
| WO | 2008131362 | A2 | 10/2008 |
| WO | 2008133956 | A2 | 11/2008 |
| WO | 2009039506 | A1 | 3/2009 |
| WO | 2007014355 | A3 | 4/2009 |
| WO | 2009132359 | A2 | 10/2009 |
| WO | 2009143092 | A1 | 11/2009 |
| WO | 2009149234 | A1 | 12/2009 |
| WO | 2011108840 | A2 | 9/2011 |
| WO | 2012/040984 | A1 | 4/2012 |
| WO | 2012040984 | A1 | 4/2012 |
| WO | 2012061640 | A1 | 5/2012 |

OTHER PUBLICATIONS

Extended European Search Report corresponding to EP 08 25 3184.9, completed Feb. 12, 2009 and mailed Feb. 27, 2009; (3 pp.).
Extended European Search Report corresponding to EP 10 25 0228.3, completed May 20, 2010 and mailed Jun. 1, 2010; (6 pp.).
Extended European Search Report corresponding to EP 10 25 2037.6, completed Mar. 1, 2011 and mailed Mar. 9, 2011; (3 pp.).
Extended European Search Report corresponding to EP 10 25 1968.3, completed on Jul. 4, 2011 and mailed Jul. 14, 2011; (12 pp.).
Extended European Search Report corresponding to EP 11 15 2266.0, completed Jul. 15, 2011 and mailed Jul. 28, 2011; (3 pp.).
Extended European Search Report corresponding to EP 11 25 0462.6, completed Jul. 20, 2011 and mailed Jul. 28, 2011; (6 pp.).
Extended European Search Report corresponding to EP 11 25 0771.0, completed Feb. 7, 2012 and mailed Feb. 17, 2012; (3 pp.).
Extended European Search Report corresponding to EP 06 78 8914.7, completed May 3, 2012 and mailed May 11, 2012; (8 pp.).
Partial European Search Report corresponding to EP 12 18 6177.7, completed Jan. 30, 2013 and mailed Feb. 12, 2013; (6 pp.).
Extended European Search Report corresponding to EP 08 25 2703.7, completed Oct. 23, 2008 and mailed Oct. 31, 2008; (7 pp.).
Extended European Search Report corresponding to EP No. 13 16 3033.7, completed Jun. 27, 2013 and mailed Jul. 15, 2013; (8 pp).
Extended European Search Report corresponding to EP No. 11 17 8021.9, mailed Jun. 4, 2013; (3 pp).
Extended European Search Report corresponding to EP No. 12 18 6177.7, completed Aug. 14, 2013 and mailed Aug. 23, 2013; (8 pp).
Partial European Search Report corresponding to EP No. 13 17 2400.7, completed Sep. 18, 2013 and mailed Oct. 1, 2013; (7 pp).
Partial European Search Report corresponding to EP No. 13 17 1742.3, completed Sep. 17, 2013 and mailed Sep. 25, 2013; (8 pp).
Extended European Search Report corresponding to EP No. 13 17 5475.6, completed Sep. 23, 2013 and mailed Oct. 1, 2013; (8 pp).
Extended European Search Report corresponding to EP No. 13 17 5478.0, completed Sep. 24, 2013 and mailed Oct. 2, 2013; (6 pp).
Extended European Search Report corresponding to EP No. 08 25 2703.7, completed Oct. 23, 2008 and mailed Oct. 31, 2008; (7 pp).
Extended European Search Report corresponding to EP No. 13 17 5479.8, completed Sep. 27, 2013 and mailed Oct. 10, 2013; (7 pp).
Partial Extended European Search Report corresponding to EP 13 17 5477.2, completed Oct. 7, 2013 and mailed Oct. 15, 2013; (7 pp).
European search Report from Appl. No. 13177163.6 dated Nov. 15, 2013. (8 pp).
Extended European Search Report from EP Application No. 13172400.7 dated Jan. 21, 2014.
Extended European Search Report from EP Application No. 13189026.1 dated Jan. 31, 2014.
The extended European Search Report from Application No. EP 13177163.6 dated Feb. 6, 2014.
Extended European Search Report from Application No. EP 13175477.2 dated Feb. 6, 2014.
Extended European Search Report from Application No. EP 13169998.5 dated Feb. 24, 2014.
Extended European Search Report corresponding to EP 13176805.3, dated Nov. 4, 2013.
Extended European Search Report from Application No. EP 13171742.3 dated Jan. 3, 2014.
Extended European Search Report from Application No. EP 13177163.6 dated Feb. 6, 2014.
Extended European Search Report corresponding to International Application No. EP 15 15 1076.5 dated Apr. 22, 2015.
Japanese Office Action corresponding to International Application No. JP 2011-084092 dated Jan. 14, 2016.
Extended European Search Report corresponding to International Application No. EP 12 19 7970.2 dated Jan. 28, 2016.
Chinese Office Action corresponding to International Application No. CN 201210560638.1 dated Oct. 21, 2015.
Australian Examination Report No. 1 corresponding to International Application No. AU 2015200153 dated Dec. 11, 2015.
Australian Examination Report No. 1 corresponding to International Application No. AU 2014204542 dated Jan. 7, 2016.
Chinese Office Action corresponding to International Application No. CN 201310125449.6 dated Feb. 3, 2016.
Extended European Search Report corresponding to International Application No. EP 15 19 0245.9 dated Jan. 28, 2016.
Extended European Search Report corresponding to International Application No. EP 15 16 7793.7 dated Apr. 5, 2016.
European Office Action corresponding to International Application No. EP 14 15 9056.2 dated Oct. 26, 2015.

(56) References Cited

OTHER PUBLICATIONS

European Office Action corresponding to International Application No. EP 14 18 4882.0 dated Apr. 25, 2016.
Extended European Search Report corresponding to International Application No. EP 14 19 6704.2 dated Sep. 24, 2015.
Extended European Search Report corresponding to International Application No. EP 14 19 7563.1 dated Aug. 5, 2015.
Partial European Search Report corresponding to International Application No. EP 15 19 0643.5 dated Feb. 26, 2016.
Extended European Search Report corresponding to International Application No. EP 15 16 6899.3 dated Feb. 3, 2016.
Extended European Search Report corresponding to International Application No. EP 14 19 9783.3 dated Dec. 22, 2015.
Extended European Search Report corresponding to International Application No. EP 15 17 3807.7 dated Nov. 24, 2015.
Extended European Search Report corresponding to International Application No. EP 15 19 0760.7 dated Apr. 1, 2016.
Extended European Search Report corresponding to International Application No. EP 15 17 3803.6 dated Nov. 24, 2015.
Extended European Search Report corresponding to International Application No. EP 15 17 3804.4 dated Nov. 24, 2015.
Extended European Search Report corresponding to International Application No. EP 15 18 8539.9 dated Feb. 17, 2016.
Extended European Search Report corresponding to International Application No. EP 15 17 3910.9 dated Nov. 13, 2015.
European Office Action corresponding to International Application No. EP 14 15 2236.7 dated Aug. 11, 2015.
Extended European Search Report corresponding to International Application No. EP 15 18 4915.5 dated Jan. 5, 2016.
International Search Report and Written Opinion corresponding to Int'l Appln. No. PCT/US2015/051837, mailed Dec. 21, 2015.
Chinese Office Action dated May 5, 2016 for application No. 2013102176333.
Extended European Search Report for Application No. 13169995.1 dated May 18, 2016.
Chinese Office Action dated May 30, 2016, issued in Chinese Application No. 201310217662.
European Search Report dated May 31, 2016, issued in European Application No. 13169993.6.
Australian Examination Report dated Oct. 24, 2016, issued in Australian Application No. 2013205875.
Australian Office Action dated Nov. 2, 2016, issued in Australian Application No. 2013205870.
Chinese Office Action dated Jan. 16, 2017, issued in CN Application No. 201310217633.
Japanese Office Action dated Feb. 14, 2017, issued in JP Appln. No. 2013-115433.
Japanese Office Action dated Mar. 28, 2017, issued in JP Application No. 2013112658.
International Search Report corresponding to PCT/US2005/027266, completed May 30, 2008 and dated Jun. 18, 2008; (2 pp.).
Extended European Search Report corresponding to EP 08 25 3184.9, completed Feb. 12, 2009 and dated Feb. 27, 2009; (3 pp.).
Extended European Search Report corresponding to EP 10 25 0228.3, completed May 20, 2010 and dated Jun. 1, 2010; (6 pp.).
Extended European Search Report corresponding to EP 10 25 2037.6, completed Mar. 1, 2011 and dated Mar. 9, 2011; (3 pp.).
Extended European Search Report corresponding to EP 10 25 1968.3, completed on Jul. 4, 2011 and dated Jul. 14, 2011; (12 pp.).
Extended European Search Report corresponding to EP 11 15 2266.0, completed Jul. 15, 2011 and dated Jul. 28, 2011; (3 pp.).
Extended European Search Report corresponding to EP 11 25 0462.6, completed Jul. 20, 2011 and dated Jul. 28, 2011; (6 pp.).
Extended European Search Report corresponding to EP 11 25 0771.0, completed Feb. 7, 2012 and dated Feb. 17, 2012; (3 pp.).
Extended European Search Report corresponding to EP 06 78 8914.7, completed May 3, 2012 and dated May 11, 2012; (8 pp.).
Partial European Search Report corresponding to EP 12 18 6177.7, completed Jan. 30, 2013 and dated Feb. 12, 2013; 6 pp.).
Extended European Search Report corresponding to EP No. 11 17 8021.9, dated Jun. 4, 2013; (3 pp).
Extended European Search Report corresponding to EP No. 13 16 3033.7, completed Jun. 27, 2013 and dated Jul. 15. 2013; (8 pp).
Extended European Search Report corresponding to EP No. 12 18 6177.7, completed Aug. 14, 2013 and dated Aug. 23, 2013; (8 pp).
Partial European Search Report corresponding to EP No. 13 17 1742.3, completed Sep. 17, 2013 and dated Sep. 25, 2013; (8 pp).
Partial European Search Report corresponding to EP No. 13 17 2400.7, completed Sep. 18, 2013 and dated Oct. 1, 2013; (7 pp).
Extended European Search Report corresponding to EP No. 13 17 5475.6, completed Sep. 23, 2013 and dated Oct. 1, 2013; (8 pp).
Extended European Search Report corresponding to EP No. 13 17 5478.0, completed Sep. 24, 2013 and dated Oct. 2, 2013; (6 pp).
Extended European Search Report corresponding to EP No. 13 17 5479.8, completed Sep. 27, 2013 and dated Oct. 10, 2013; (7 pp).
Partial Extended European Search Report corresponding to EP 13 17 5477.2, completed Oct. 7, 2013 and dated Oct. 15, 2013; (7 pp).
Extended European Search Report corresponding to EP No. 08 25 2703.7, completed Oct. 23, 2008 and dated Oct. 31, 2008; (7 pp).
International Search Report and Written Opinion corresponding to Int'l Appln. No. PCT/US2015/051837, dated Dec. 21, 2015.
Extended European Search Report dated Oct. 14, 2019 issued in corresponding EP Appln. No. 19178144.2.
Australian Patent Examination Report No. 1, dated Jan. 7, 2016, corresponding to Australian Patent Application No. 2014204542; 4 pages.
Extended European Search Report corresponding to EP 08 25 2703.7, completed Oct. 23, 2008 and dated Oct. 31, 2008; (7 pp.).

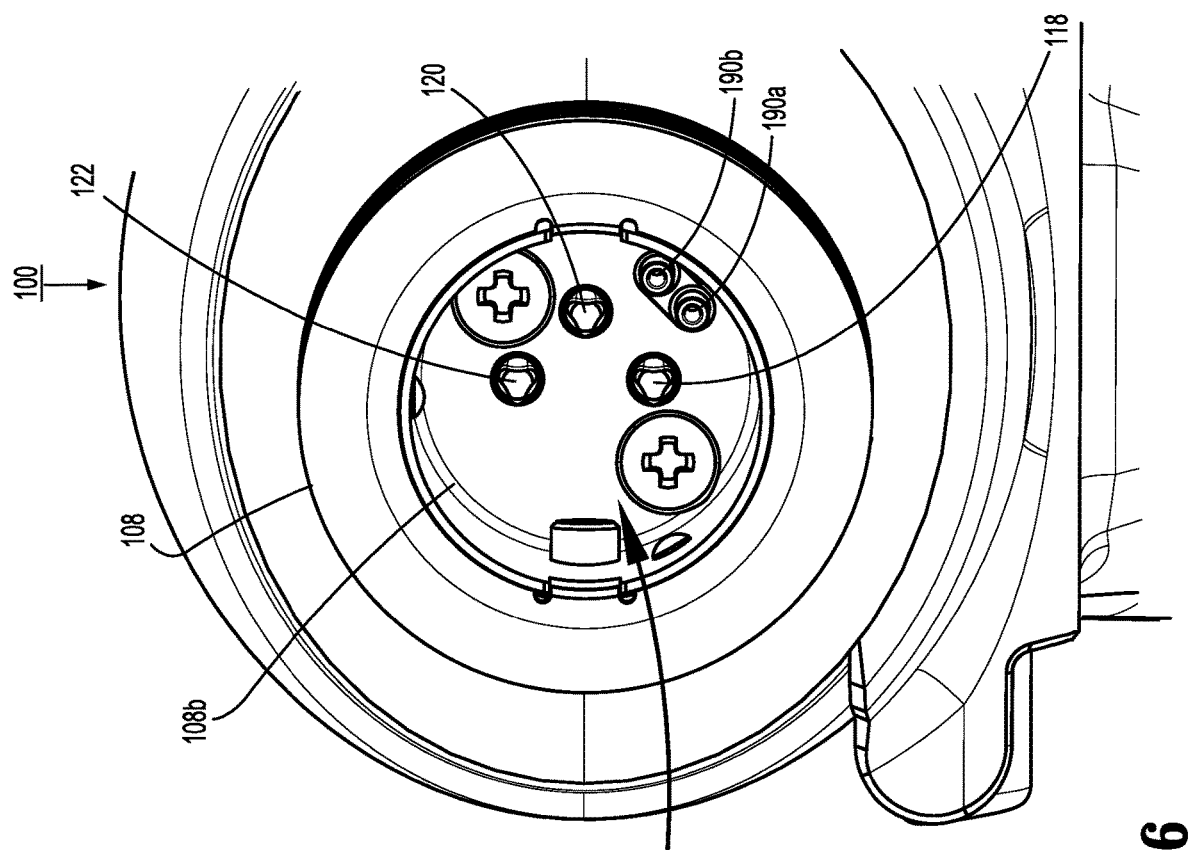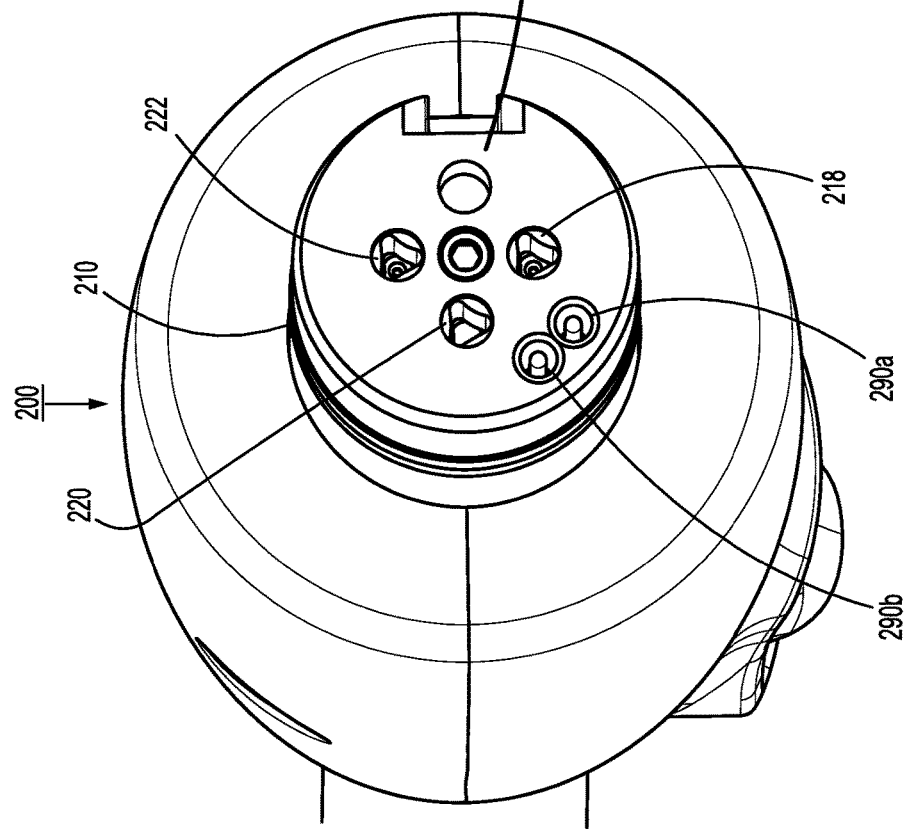
FIG. 6

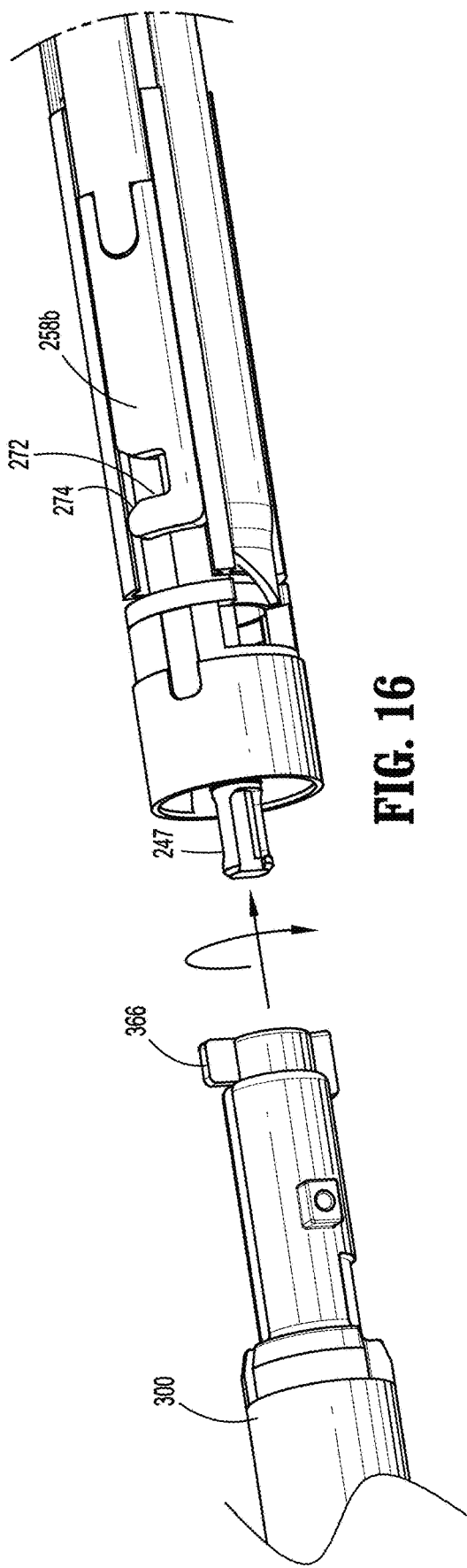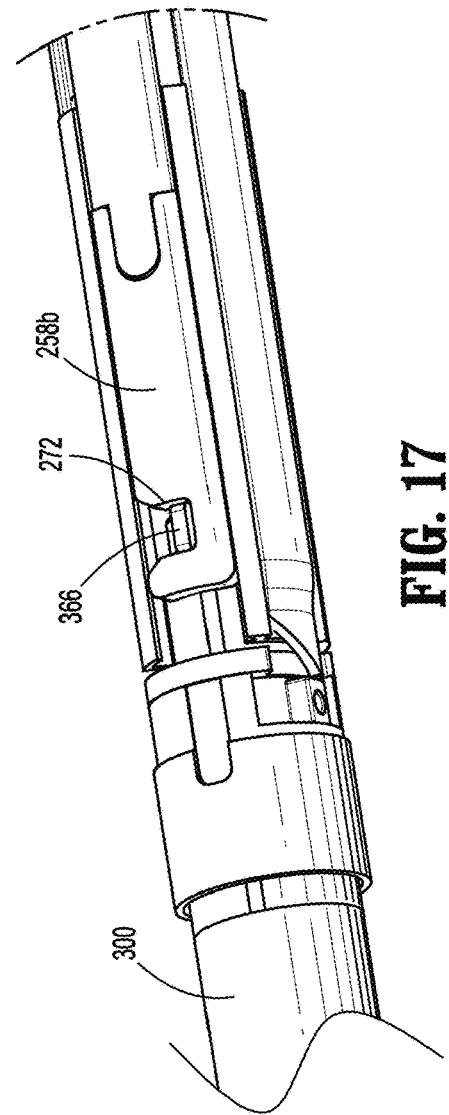

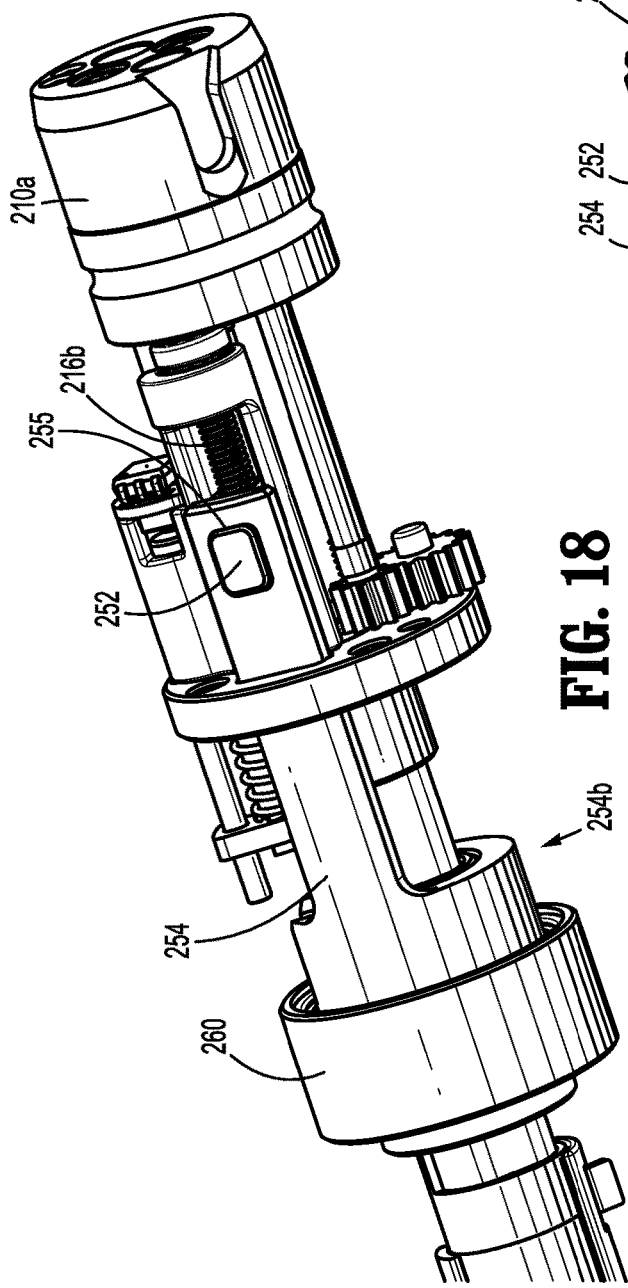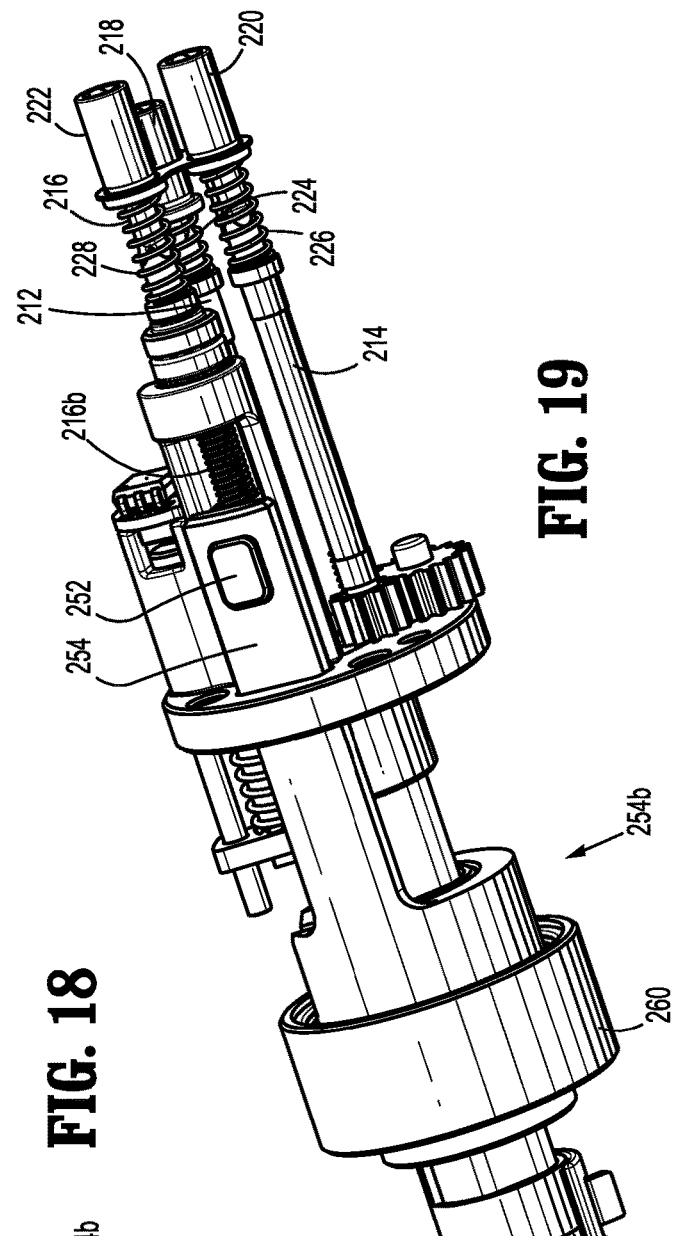

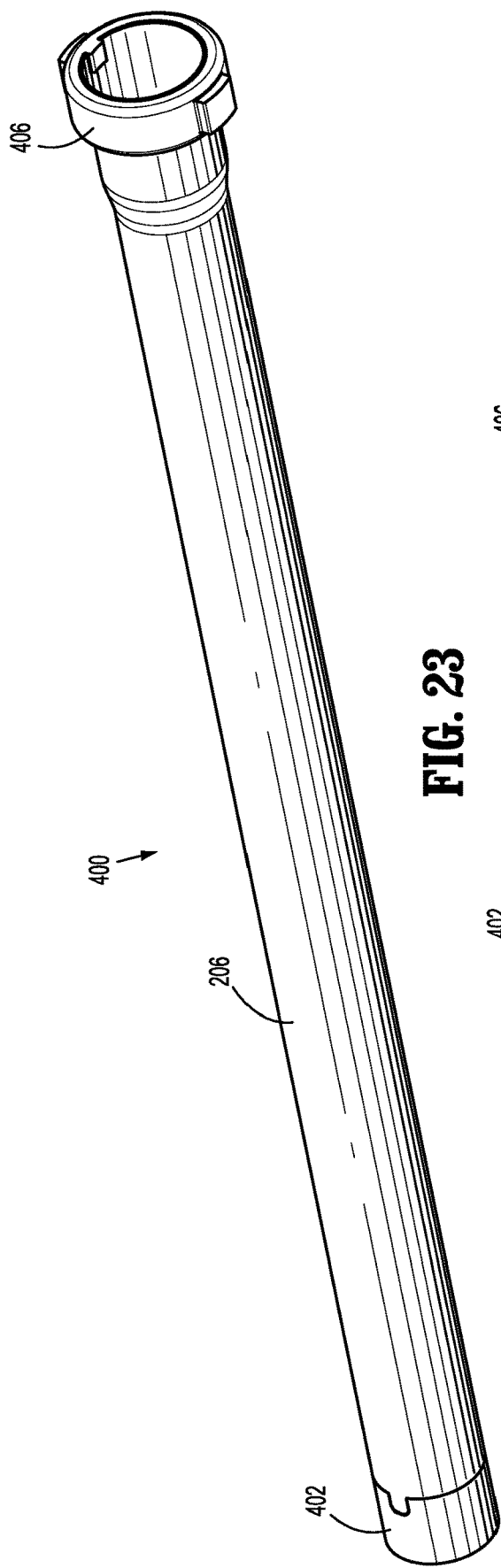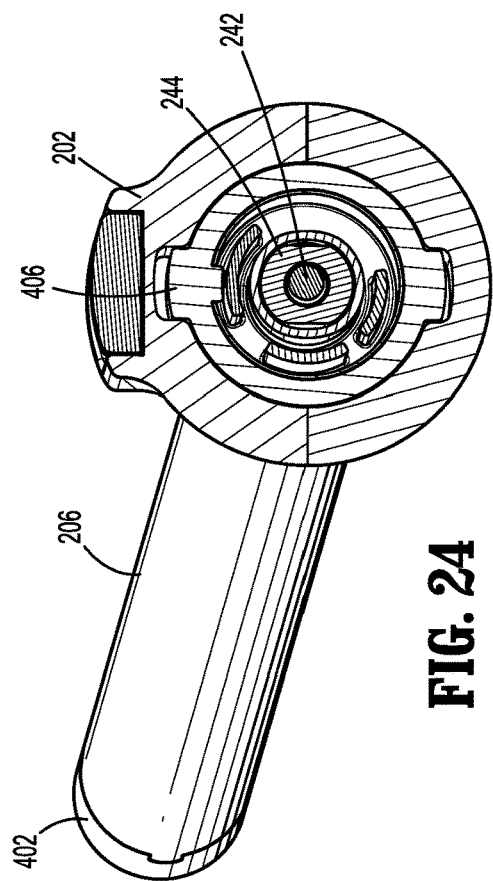
FIG. 23
FIG. 24

HANDHELD SURGICAL HANDLE ASSEMBLY, SURGICAL ADAPTERS FOR USE BETWEEN SURGICAL HANDLE ASSEMBLY AND SURGICAL END EFFECTORS, AND METHODS OF USE

CROSS-REFERENCE TO RELATED APPLICATIONS

This application is a continuation of U.S. patent application Ser. No. 16/773,798, filed Jan. 27, 2020, which is a continuation of U.S. patent application Ser. No. 15/451,472 filed Mar. 7, 2017, now U.S. Pat. No. 10,542,984, which is a continuation of U.S. patent application Ser. No. 13/875,571, filed May 2, 2013, now U.S. Pat. No. 9,597,104, which claims the benefit of and priority to, U.S. Provisional Patent Application No. 61/654,191, filed Jun. 1, 2012. The entire contents of each of the foregoing applications are hereby incorporated by reference herein.

BACKGROUND

1. Technical Field

The present disclosure relates to surgical devices and/or systems, surgical adapters and their methods of use. More specifically, the present disclosure relates to hand held powered surgical devices, surgical adapters and/or adapter assemblies for use between and for interconnecting the powered, rotating and/or articulating surgical device or handle assembly and an end effector for clamping, cutting and/or stapling tissue.

2. Background of Related Art

One type of surgical device is a linear clamping, cutting and stapling device. Such a device may be employed in a surgical procedure to resect a cancerous or anomalous tissue from a gastro-intestinal tract. Conventional linear clamping, cutting and stapling instruments include a pistol grip-styled structure having an elongated shaft and distal portion. The distal portion includes a pair of scissors-styled gripping elements, which clamp the open ends of the colon closed. In this device, one of the two scissors-styled gripping elements, such as the anvil portion, moves or pivots relative to the overall structure, whereas the other gripping element remains fixed relative to the overall structure. The actuation of this scissoring device (the pivoting of the anvil portion) is controlled by a grip trigger maintained in the handle.

In addition to the scissoring device, the distal portion also includes a stapling mechanism. The fixed gripping element of the scissoring mechanism includes a staple cartridge receiving region and a mechanism for driving the staples up through the clamped end of the tissue against the anvil portion, thereby sealing the previously opened end. The scissoring elements may be integrally formed with the shaft or may be detachable such that various scissoring and stapling elements may be interchangeable.

A number of surgical device manufacturers have developed product lines with proprietary drive systems for operating and/or manipulating the surgical device. In many instances the surgical devices include a handle assembly, which is reusable, and a disposable end effector or the like that is selectively connected to the handle assembly prior to use and then disconnected from the end effector following use in order to be disposed of or in some instances sterilized for re-use.

Many of the existing end effectors for use with many of the existing surgical devices and/or handle assemblies are driven by a linear force. For examples, end effectors for performing endo-gastrointestinal anastomosis procedures, end-to-end anastomosis procedures and transverse anastomosis procedures, each typically require a linear driving force in order to be operated. As such, these end effectors are not compatible with surgical devices and/or handle assemblies that use a rotary motion to deliver power or the like.

In order to make the linear driven end effectors compatible with surgical devices and/or handle assemblies that use a rotary motion to deliver power, a need exists for adapters and/or adapter assemblies to interface between and interconnect the linear driven end effectors with the rotary driven surgical devices and/or handle assemblies.

SUMMARY

The present disclosure relates to a surgical device comprising a device housing, at last one drive motor, a battery, a circuit board, an end effector, and an adapter assembly. The device housing defines a connecting portion for selectively connecting with the adapter assembly. The at least one drive motor is supported in the device housing and is configured to rotate at least one drive shaft. The battery is disposed in electrical communication with the at least one drive motor. The circuit board is disposed within the housing for controlling power delivered from the battery to the at least one drive motor. The end effector is configured to perform at least one function and includes at least one axially translatable drive member. The adapter assembly is for selectively interconnecting the end effector and the device housing, and includes a knob housing, and at least one drive converter assembly. The knob housing is configured and adapted for selective connection to the device housing and to be in operative communication with each of the at least one rotatable drive shaft. The at least one drive converter assembly is for interconnecting a respective one of the at least one rotatable drive shaft and one of the at least one axially translatable drive member of the end effector. The at least one drive converter assembly converts and transmits a rotation of the rotatable drive shaft to an axial translation of the at least one axially translatable drive member of the end effector. The at least one drive converter assembly includes a first drive converter assembly including a first drive element, a nut, an articulation sleeve, an articulation bearing, and an articulation link. The first drive element is rotatably supported in the knob housing. A proximal end of the first drive element is engagable with the rotatable drive shaft. The nut is threadably connected to a threaded distal portion of the first drive element. A proximal portion of the articulation sleeve is disposed in mechanical cooperation with the nut. The articulation bearing is disposed in mechanical cooperation with a distal portion of the articulation sleeve. A proximal portion of the articulation link is disposed in mechanical cooperation with the articulation bearing. A distal portion of the articulation link is configured for selective engagement with the at least one axially translatable drive member of the end effector. Rotation of the rotatable drive shaft results in rotation of the first drive element. Rotation of the first drive element results in axial translation of the nut, the articulation sleeve, the articulation bearing, the articulation link, and the at least one axially translatable drive member of the end effector.

In disclosed embodiments, the articulation bearing is configured for axial and rotatable movement with respect to the knob housing.

In disclosed embodiments, the distal portion of the articulation sleeve is disposed in mechanically cooperation with a radially inner portion of the articulation bearing. Here, it is disclosed that the proximal portion of the articulation link is disposed in mechanical cooperation with a radially outer portion of the articulation bearing.

In disclosed embodiments, a second drive converter assembly is included and comprises a second drive element, a first gear, a second gear, and a gear ring. The second drive element is rotatably supported in the knob housing. A proximal end of the second drive element is connectable to a second rotatable drive shaft of the surgical device. The first gear is disposed in mechanical cooperation with a distal portion of the second drive element. The second gear is disposed in mechanical cooperation with the first gear. The gear ring is disposed in mechanical cooperation with the second gear and is disposed in mechanical cooperation with the end effector. The gear ring is fixed from rotation with respect to the knob housing. Rotation of the second rotatable drive shaft causes rotation of the first gear, rotation of the first gear causes rotation of the second gear, rotation of the second gear causes rotation of the gear ring, and rotation of the gear ring causes rotation of the end effector. Here, it is disclosed that the knob housing includes a drive coupling housing, which is rotatable with respect to the remainder of the knob housing. Here, it is disclosed that a rotation bearing is included, and the drive coupling housing is rotationally fixed to the rotation bearing. The knob housing is rotatable with respect to the rotation bearing. Here, it is disclosed that the gear ring includes a plurality of teeth disposed around an inner periphery thereof.

In disclosed embodiments, a distal portion of the articulation link includes a slot therein configured to releasably accept a portion of the at least one axially translatable drive member of the end effector. Here, it is disclosed that the slot includes a tapered opening.

The present disclosure also relates to an adapter assembly for selectively interconnecting a surgical end effector and a handle assembly having at least one rotatable drive shaft. The adapter assembly comprises a knob housing, ant at least one drive converter assembly. The knob housing is configured and adapted for selective connection to a handle assembly. The knob housing includes a drive coupling housing. The at least one drive converter assembly is for interconnecting a respective one of the at least one rotatable drive shaft and a portion of a surgical end effector. The at least one drive converter assembly converts and transmits a rotation of the rotatable drive shaft to an axial translation of the at least one axially translatable drive member of the end effector. The at least one drive converter assembly includes a first drive converter assembly including a drive element, a first gear, a second gear, a gear ring and a rotation bearing. The drive element is rotatably supported in the adapter housing. The first gear is disposed in mechanical cooperation with a distal portion of the drive element. The second gear is disposed in mechanical cooperation with the first gear. The gear ring is disposed in mechanical cooperation with the second gear and is disposed in mechanical cooperation with an end effector-engaging portion of the adapter assembly. The gear ring is fixed from rotation with respect to the adapter housing. The drive coupling housing is rotationally fixed to the rotation bearing, and the knob housing is rotatable with respect to the rotation bearing. Rotation of the drive element causes rotation of the first gear; rotation of the first gear causes rotation of the second gear; rotation of the second gear causes rotation of the gear ring; and rotation of the gear ring causes rotation of the end effector-engaging portion of the adapter assembly.

In disclosed embodiments, the gear ring includes a plurality of teeth disposed around an inner periphery thereof.

In disclosed embodiments, the drive coupling housing is rotatable with respect to the remainder of the knob housing.

In disclosed embodiments, a second drive converter assembly is included and comprises a second drive element, a nut, an articulation sleeve, and an articulation link. The second drive element is rotatably supported in the knob housing. The nut is threadably connected to a threaded distal portion of the second drive element. A proximal portion of the articulation sleeve is disposed in mechanical cooperation with the nut. The articulation bearing is disposed in mechanical cooperation with a distal portion of the articulation sleeve. A proximal portion of the articulation link is disposed in mechanical cooperation with the articulation bearing. A distal portion of the articulation link is configured for selective engagement with a portion of an end effector. Rotation of the second drive element results in axial translation of the nut, the articulation sleeve, the articulation bearing and the articulation link. Here, it is disclosed that the articulation bearing is configured for axial and rotatable movement with respect to the knob housing. Here, it is disclosed that distal portion of the articulation sleeve is disposed in mechanically cooperation with a radially inner portion of the articulation bearing. Here, it is disclosed that the proximal portion of the articulation link is disposed in mechanical cooperation with a radially outer portion of the articulation bearing.

BRIEF DESCRIPTION OF THE DRAWINGS

Embodiments of the present disclosure are described herein with reference to the accompanying drawings, wherein:

FIG. 6 is a perspective view of the connecting ends of each of the surgical device and the adapter, illustrating a connection therebetween;

FIG. 16 is an enlarged view of the indicated area of detail of FIG. 14;

FIG. 17 is a perspective view of the distal end of the adapter engaged with a loading unit;

FIGS. 18 and 19 are perspective views of portions of the adapter with parts omitted;

FIG. 23 is a perspective view of a distal portion of the adapter;

FIG. 24 is a cut-away perspective view looking distally at the distal portion of the adapter as shown in FIG. 23;

DETAILED DESCRIPTION OF EMBODIMENTS

Figure 1:
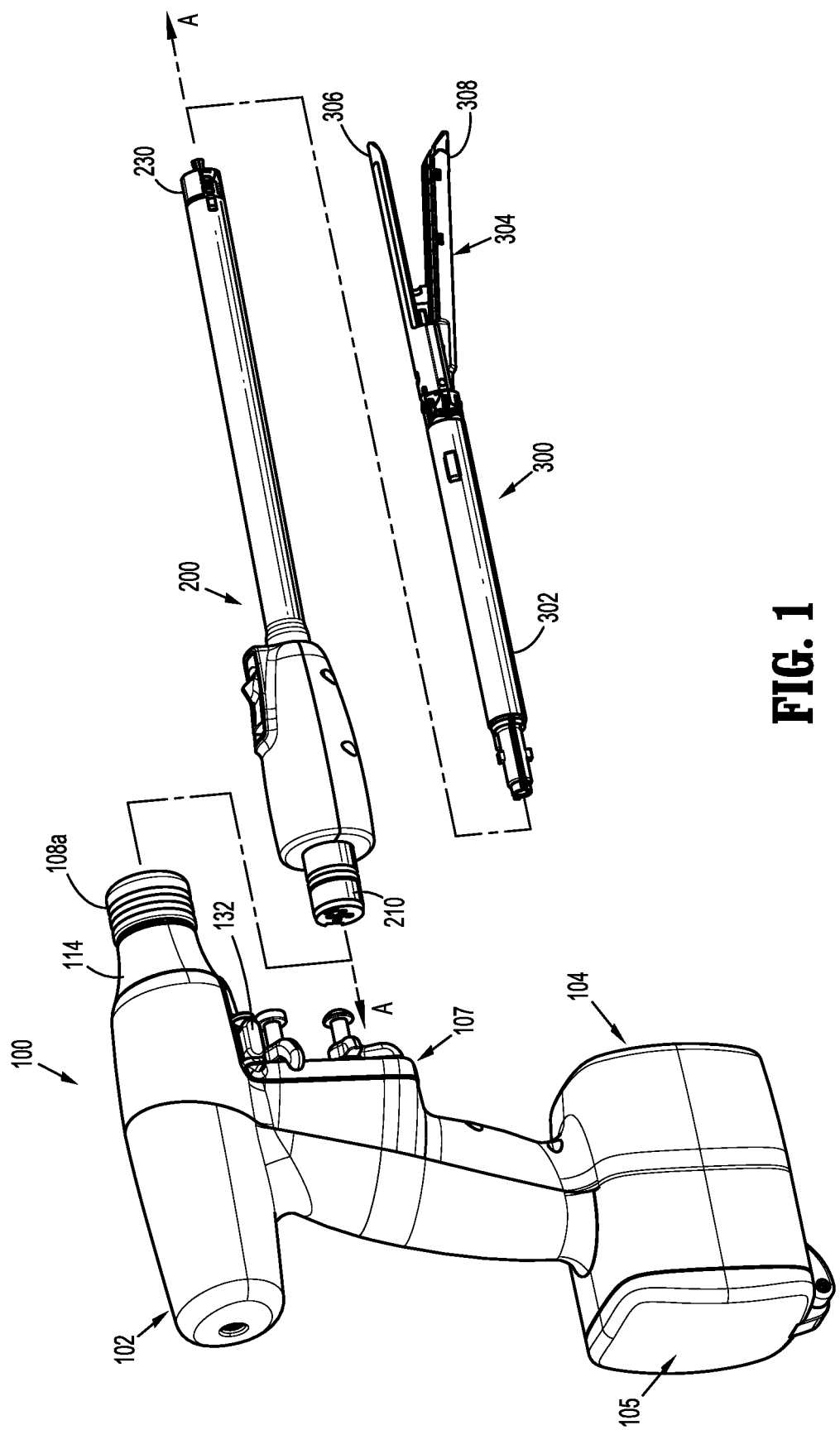
FIG. 1 is a perspective view, with parts separated, of a surgical device and adapter, in accordance with an embodiment of the present disclosure, illustrating a connection thereof with an end effector.

Embodiments of the presently disclosed surgical devices, and adapter assemblies for surgical devices and/or handle assemblies are described in detail with reference to the drawings, in which like reference numerals designate identical or corresponding elements in each of the several views. As used herein the term "distal" refers to that portion of the adapter assembly or surgical device, or component thereof, farther from the user, while the term "proximal" refers to that portion of the adapter assembly or surgical device, or component thereof, closer to the user.

A surgical device, in accordance with an embodiment of the present disclosure, is generally designated as 100, and is in the form of a powered hand held electromechanical instrument configured for selective attachment thereto of a plurality of different end effectors that are each configured for actuation and manipulation by the powered hand held electromechanical surgical instrument.

As illustrated in FIG. 1, surgical device 100 is configured for selective connection with an adapter 200, and, in turn, adapter 200 is configured for selective connection with an end effector or single use loading unit 300.

Figure 2:
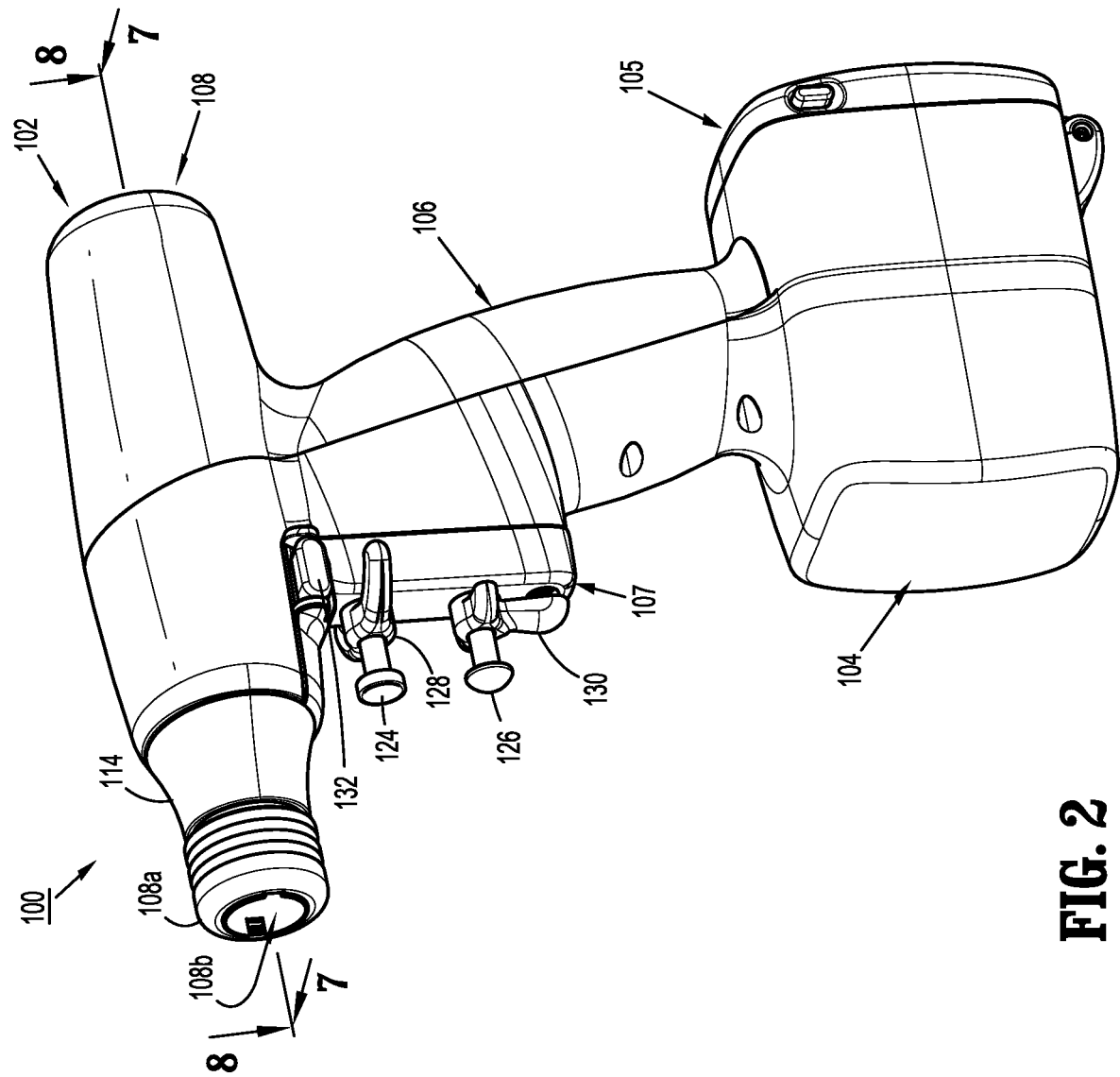
FIG. 2 is a perspective view of the surgical device of FIG. 1.
Figure 3:
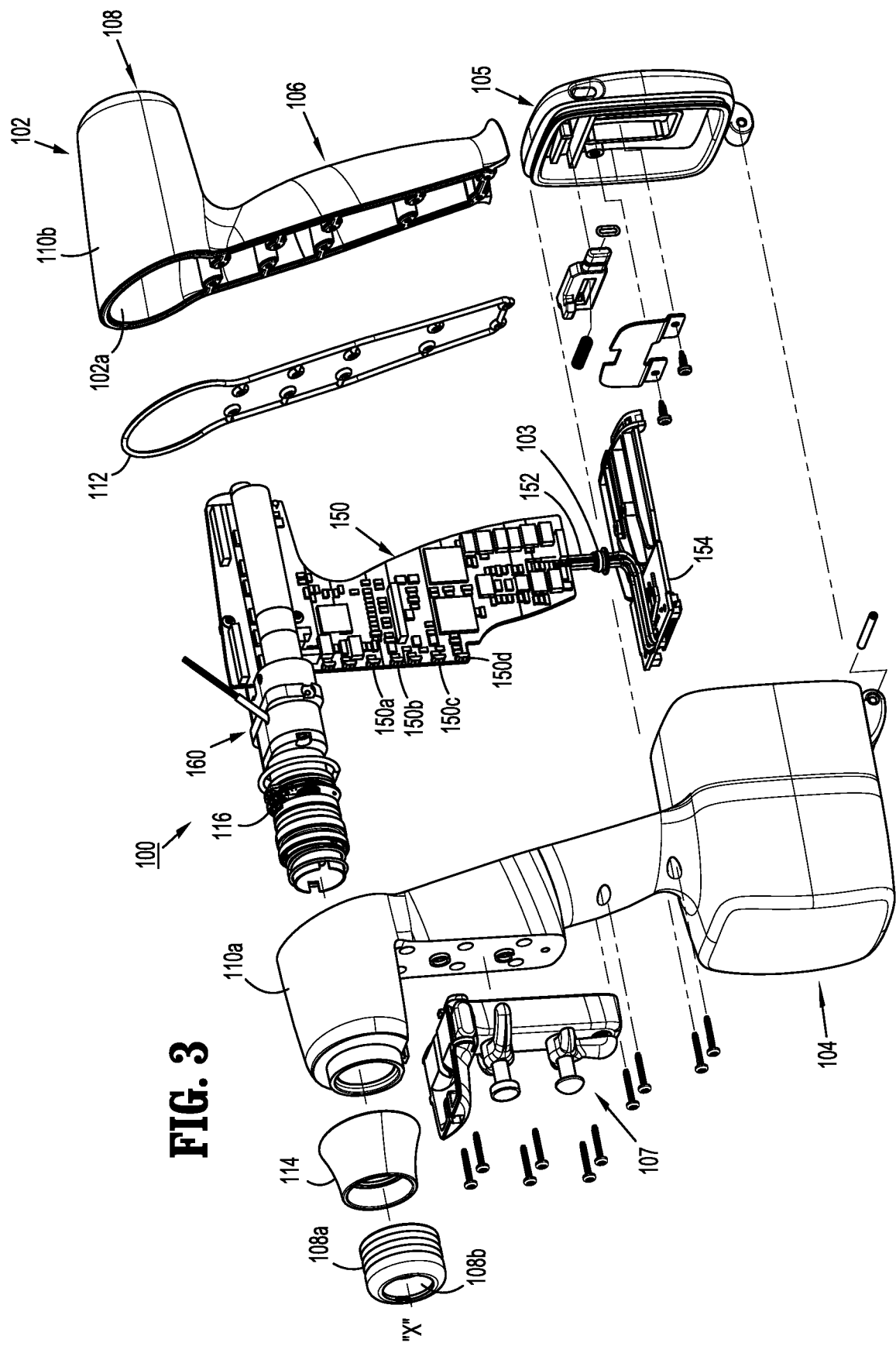
FIG. 3 is a perspective view, with parts separated, of the surgical device of FIGS. 1 and 2.

As illustrated in FIGS. 1-3, surgical device 100 includes a handle housing 102 having a lower housing portion 104, an intermediate housing portion 106 extending from and/or supported on lower housing portion 104, and an upper housing portion 108 extending from and/or supported on intermediate housing portion 106. Intermediate housing portion 106 and upper housing portion 108 are separated into a distal half-section 110a that is integrally formed with and extending from the lower portion 104, and a proximal half-section 110b connectable to distal half-section 110a by a plurality of fasteners. When joined, distal and proximal half-sections 110a, 110b define a handle housing 102 having a cavity 102a therein in which a circuit board 150 and a drive mechanism 160 is situated.

Distal and proximal half-sections 110a, 110b are divided along a plane that traverses a longitudinal axis "X" of upper housing portion 108, as seen in FIG. 3.

Handle housing 102 includes a gasket 112 extending completely around a rim of distal half-section and/or proximal half-section 110a, 110b and being interposed between distal half-section 110a and proximal half-section 110b. Gasket 112 seals the perimeter of distal half-section 110a and proximal half-section 110b. Gasket 112 functions to establish an air-tight seal between distal half-section 110a and proximal half-section 110b such that circuit board 150 and drive mechanism 160 are protected from sterilization and/or cleaning procedures.

In this manner, the cavity 102a of handle housing 102 is sealed along the perimeter of distal half-section 110a and proximal half-section 110b yet is configured to enable easier, more efficient assembly of circuit board 150 and a drive mechanism 160 in handle housing 102.

Intermediate housing portion 106 of handle housing 102 provides a housing in which circuit board 150 is situated. Circuit board 150 is configured to control the various operations of surgical device 100, as will be set forth in additional detail below.

Figure 4:
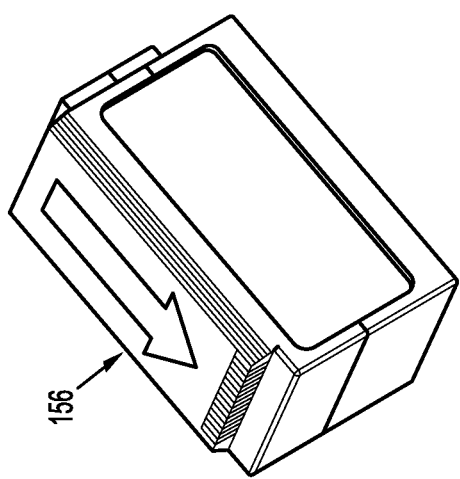
FIG. 4 is a perspective view of a battery for use in the surgical device of FIGS. 1-3.

Lower housing portion 104 of surgical device 100 defines an aperture (not shown) formed in an upper surface thereof and which is located beneath or within intermediate housing portion 106. The aperture of lower housing portion 104 provides a passage through which wires 152 pass to electrically interconnect electrical components (a battery 156, as illustrated in FIG. 4, a circuit board 154, as illustrated in FIG. 3, etc.) situated in lower housing portion 104 with electrical components (circuit board 150, drive mechanism 160, etc.) situated in intermediate housing portion 106 and/or upper housing portion 108.

Handle housing 102 includes a gasket 103 disposed within the aperture of lower housing portion 104 (not shown) thereby plugging or sealing the aperture of lower housing portion 104 while allowing wires 152 to pass therethrough. Gasket 103 functions to establish an air-tight seal between lower housing portion 106 and intermediate housing portion 108 such that circuit board 150 and drive mechanism 160 are protected from sterilization and/or cleaning procedures.

As shown, lower housing portion 104 of handle housing 102 provides a housing in which a rechargeable battery 156, is removably situated. Battery 156 is configured to supply power to any of the electrical components of surgical device 100. Lower housing portion 104 defines a cavity (not shown) into which battery 156 is inserted. Lower housing portion 104 includes a door 105 pivotally connected thereto for closing cavity of lower housing portion 104 and retaining battery 156 therein.

Figure 5:
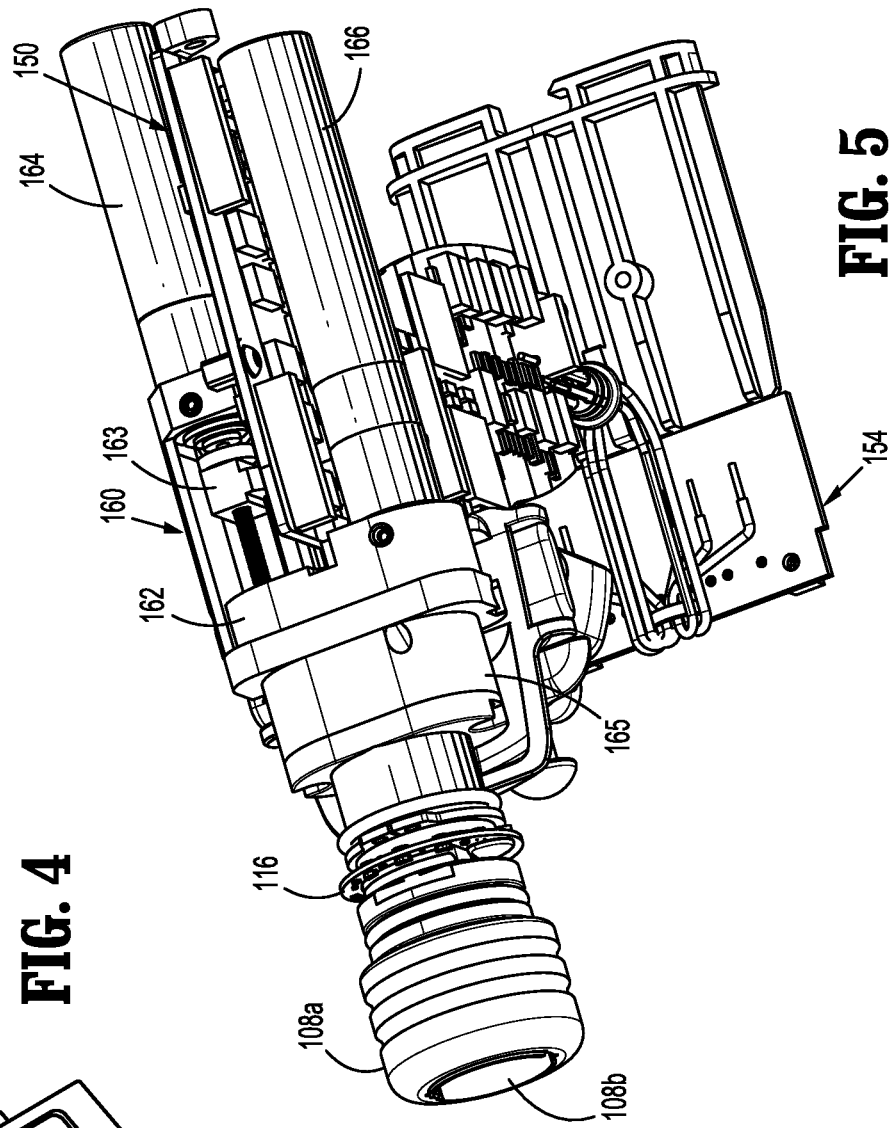
FIG. 5 is a perspective view of the surgical device of FIGS. 1-3, with a housing thereof removed.

With reference to FIGS. 3 and 5, distal half-section 110a of upper housing portion 108 defines a nose or connecting portion 108a. A nose cone 114 is supported on nose portion 108a of upper housing portion 108. Nose cone 114 is fabricated from a transparent material. An illumination member 116 is disposed within nose cone 114 such that illumination member 116 is visible therethrough. Illumination member 116 is in the form of a light emitting diode printed circuit board (LED PCB). Illumination member 116 is configured to illuminate multiple colors with a specific color pattern being associated with a unique discrete event.

Upper housing portion 108 of handle housing 102 provides a housing in which drive mechanism 160 is situated. As illustrated in FIG. 5, drive mechanism 160 is configured to drive shafts and/or gear components in order to perform the various operations of surgical device 100. In particular, drive mechanism 160 is configured to drive shafts and/or gear components in order to selectively move tool assembly 304 of end effector 300 (see FIGS. 1 and 20) relative to proximal body portion 302 of end effector 300, to rotate end effector 300 about a longitudinal axis "X" (see FIG. 3) relative to handle housing 102, to move anvil assembly 306 relative to cartridge assembly 308 of end effector 300, and/or to fire a stapling and cutting cartridge within cartridge assembly 308 of end effector 300.

The drive mechanism 160 includes a selector gearbox assembly 162 that is located immediately proximal relative to adapter 200. Proximal to the selector gearbox assembly 162 is a function selection module 163 having a first motor 164 that functions to selectively move gear elements within the selector gearbox assembly 162 into engagement with an input drive component 165 having a second motor 166.

As illustrated in FIGS. 1-4, and as mentioned above, distal half-section 110*a* of upper housing portion 108 defines a connecting portion 108*a* configured to accept a corresponding drive coupling assembly 210 of adapter 200.

Figure 7:
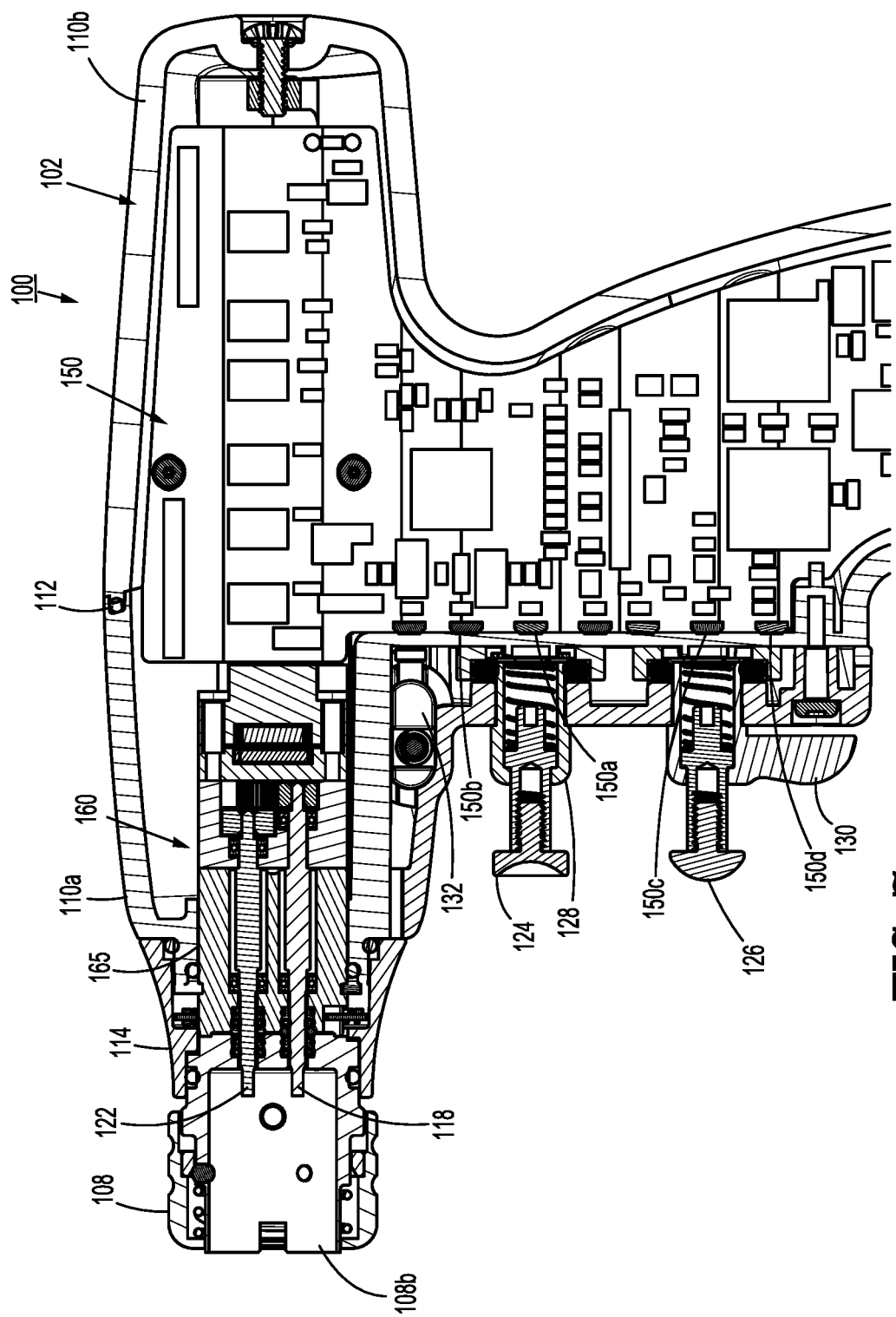
FIG. 7 is a cross-sectional view of the surgical device of FIGS. 1-3, as taken through 7-7 of FIG. 2.
Figure 8:
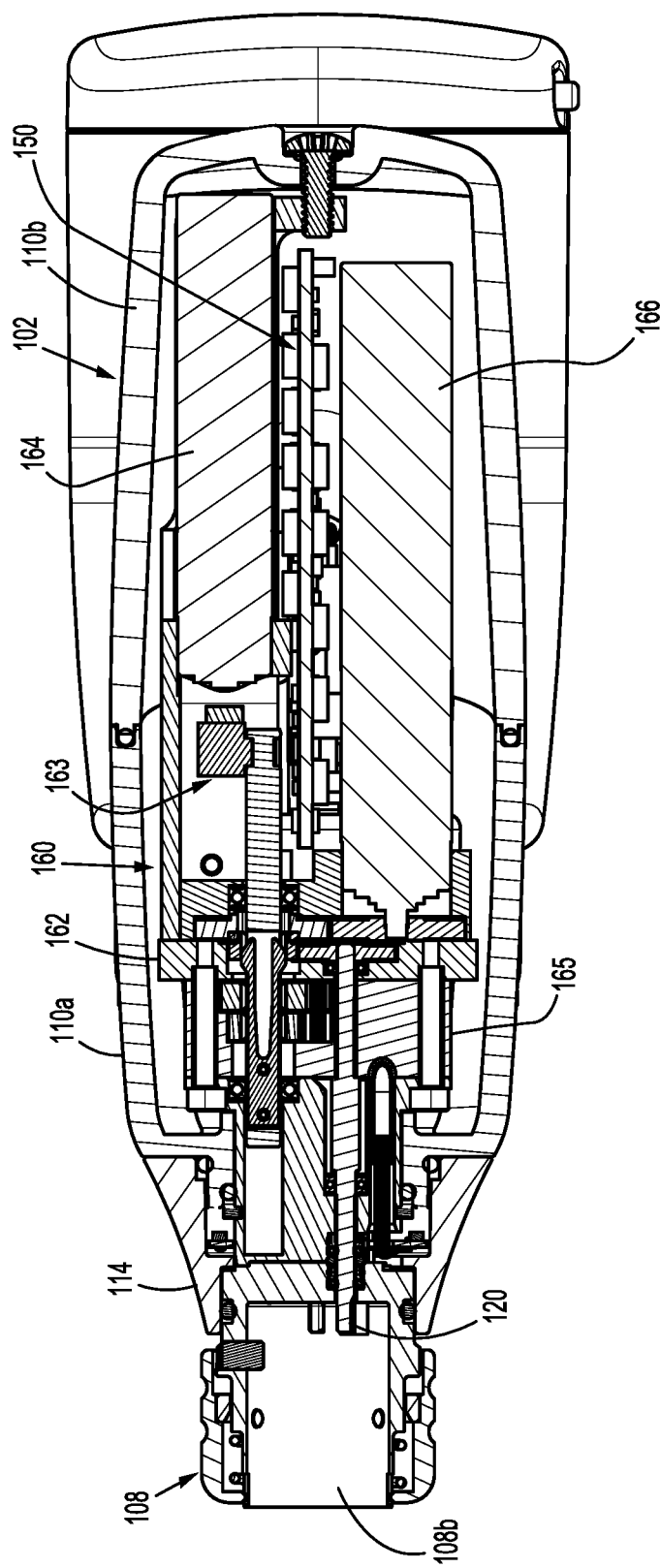
FIG. 8 is a cross-sectional view of the surgical device of FIGS. 1-3, as taken through 8-8 of FIG. 2.
Figure 9:
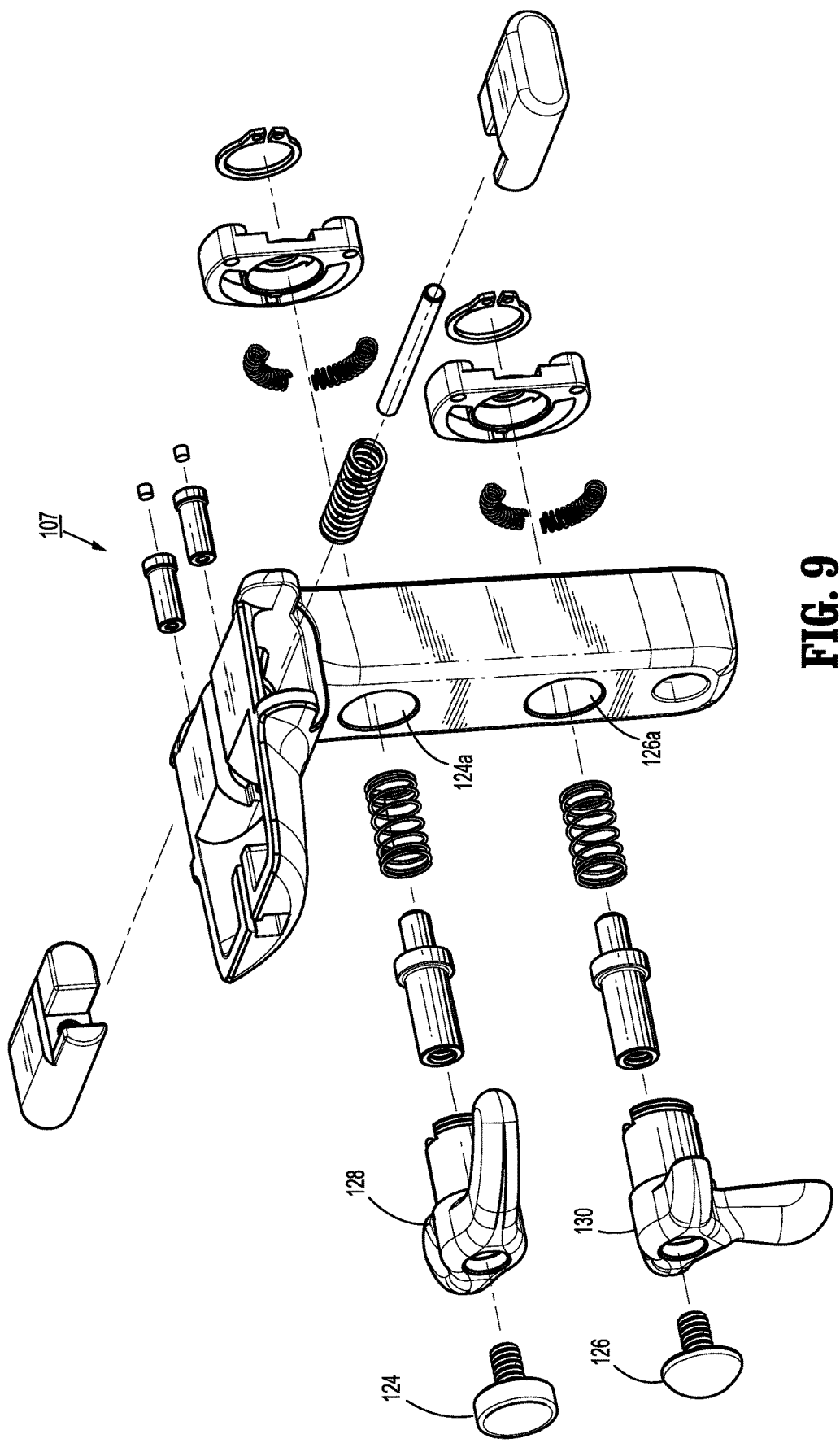
FIG. 9 is a perspective view, with parts separated, of a trigger housing of the surgical device of FIGS. 1-3.

As illustrated in FIGS. 6-8, connecting portion 108*a* of surgical device 100 has a cylindrical recess 108*b* that receives a drive coupling assembly 210 of adapter 200 when adapter 200 is mated to surgical device 100. Connecting portion 108*a* houses three rotatable drive connectors 118, 120, 122.

When adapter 200 is mated to surgical device 100, each of rotatable drive connectors 118, 120, 122 of surgical device 100 couples with a corresponding rotatable connector sleeve 218, 220, 222 of adapter 200. (see FIG. 6). In this regard, the interface between corresponding first drive connector 118 and first connector sleeve 218, the interface between corresponding second drive connector 120 and second connector sleeve 220, and the interface between corresponding third drive connector 122 and third connector sleeve 222 are keyed such that rotation of each of drive connectors 118, 120, 122 of surgical device 100 causes a corresponding rotation of the corresponding connector sleeve 218, 220, 222 of adapter 200.

The mating of drive connectors 118, 120, 122 of surgical device 100 with connector sleeves 218, 220, 222 of adapter 200 allows rotational forces to be independently transmitted via each of the three respective connector interfaces. The drive connectors 118, 120, 122 of surgical device 100 are configured to be independently rotated by drive mechanism 160. In this regard, the function selection module 163 of drive mechanism 160 selects which drive connector or connectors 118, 120, 122 of surgical device 100 is to be driven by the input drive component 165 of drive mechanism 160.

Since each of drive connectors 118, 120, 122 of surgical device 100 has a keyed and/or substantially non-rotatable interface with respective connector sleeves 218, 220, 222 of adapter 200, when adapter 200 is coupled to surgical device 100, rotational force(s) are selectively transferred from drive mechanism 160 of surgical device 100 to adapter 200.

The selective rotation of drive connector(s) 118, 120 and/or 122 of surgical device 100 allows surgical device 100 to selectively actuate different functions of end effector 300. As will be discussed in greater detail below, selective and independent rotation of first drive connector 118 of surgical device 100 corresponds to the selective and independent opening and closing of tool assembly 304 of end effector 300, and driving of a stapling/cutting component of tool assembly 304 of end effector 300. Also, the selective and independent rotation of second drive connector 120 of surgical device 100 corresponds to the selective and independent articulation of tool assembly 304 of end effector 300 transverse to longitudinal axis "X" (see FIG. 3). Additionally, the selective and independent rotation of third drive connector 122 of surgical device 100 corresponds to the selective and independent rotation of end effector 300 about longitudinal axis "X" (see FIG. 3) relative to handle housing 102 of surgical device 100.

As mentioned above and as illustrated in FIGS. 5 and 8, drive mechanism 160 includes a selector gearbox assembly 162; a function selection module 163, located proximal to the selector gearbox assembly 162, that functions to selectively move gear elements within the selector gearbox assembly 162 into engagement with second motor 166. Thus, drive mechanism 160 selectively drives one of drive connectors 118, 120, 122 of surgical device 100 at a given time.

As illustrated in FIGS. 1-3 and FIG. 9, handle housing 102 supports a trigger housing 107 on a distal surface or side of intermediate housing portion 108. Trigger housing 107, in cooperation with intermediate housing portion 108, supports a pair of finger-actuated control buttons 124, 126 and rocker devices 128, 130. In particular, trigger housing 107 defines an upper aperture 124*a* for slidably receiving a first control button 124, and a lower aperture 126*b* for slidably receiving a second control button 126.

Each one of the control buttons 124, 126 and rocker devices 128, 130 includes a respective magnet (not shown) that is moved by the actuation of an operator. In addition, circuit board 150 includes, for each one of the control buttons 124, 126 and rocker devices 128, 130, respective Hall-effect switches 150*a*-150*d* that are actuated by the movement of the magnets in the control buttons 124, 126 and rocker devices 128, 130. In particular, located immediately proximal to the control button 124 is a first Hall-effect switch 150*a* (see FIGS. 3 and 7) that is actuated upon the movement of a magnet within the control button 124 upon the operator actuating control button 124. The actuation of first Hall-effect switch 150*a*, corresponding to control button 124, causes circuit board 150 to provide appropriate signals to function selection module 163 and input drive component 165 of the drive mechanism 160 to close a tool assembly 304 of end effector 300 and/or to fire a stapling/cutting cartridge within tool assembly 304 of end effector 300.

Also, located immediately proximal to rocker device 128 is a second Hall-effect switch 150*b* (see FIGS. 3 and 7) that is actuated upon the movement of a magnet (not shown) within rocker device 128 upon the operator actuating rocker device 128. The actuation of second Hall-effect switch 150*b*, corresponding to rocker device 128, causes circuit board 150 to provide appropriate signals to function selection module 163 and input drive component 165 of drive mechanism 160 to articulate tool assembly 304 relative to body portion 302 of end effector 300. Advantageously, movement of rocker device 128 in a first direction causes tool assembly 304 to articulate relative to body portion 302 in a first direction, while movement of rocker device 128 in an opposite, e.g., second, direction causes tool assembly 304 to articulate relative to body portion 302 in an opposite, e.g., second, direction.

Furthermore, located immediately proximal to control button 126 is a third Hall-effect switch 150*c* (see FIGS. 3 and 7) that is actuated upon the movement of a magnet (not shown) within control button 126 upon the operator actuating control button 126. The actuation of third Hall-effect switch 150*c*, corresponding to control button 126, causes circuit board 150 to provide appropriate signals to function selection module 163 and input drive component 165 of drive mechanism 160 to open tool assembly 304 of end effector 300.

In addition, located immediately proximal to rocker device 130 is a fourth Hall-effect switch 150*d* (see FIGS. 3 and 7) that is actuated upon the movement of a magnet (not shown) within rocker device 130 upon the operator actuating rocker device 130. The actuation of fourth Hall-effect switch 150*d*, corresponding to rocker device 130, causes circuit board 150 to provide appropriate signals to function selection module 163 and input drive component 165 of drive mechanism 160 to rotate end effector 300 relative to handle housing 102 surgical device 100. Specifically, movement of rocker device 130 in a first direction causes end effector 300 to rotate relative to handle housing 102 in a first direction, while movement of rocker device 130 in an opposite, e.g., second, direction causes end effector 300 to rotate relative to handle housing 102 in an opposite, e.g., second, direction.

As seen in FIGS. 1-3, surgical device 100 includes a fire button or safety switch 132 supported between intermediate housing portion 108 and upper housing portion, and situated above trigger housing 107. In use, tool assembly 304 of end effector 300 is actuated between opened and closed conditions as needed and/or desired. In order to fire end effector 300, to expel fasteners therefrom when tool assembly 304 of end effector 300 is in a closed condition, safety switch 132 is depressed thereby instructing surgical device 100 that end effector 300 is ready to expel fasteners therefrom.

As illustrated in FIGS. 1 and 10-25, surgical device 100 is configured for selective connection with adapter 200, and, in turn, adapter 200 is configured for selective connection with end effector 300.

Figure 26:
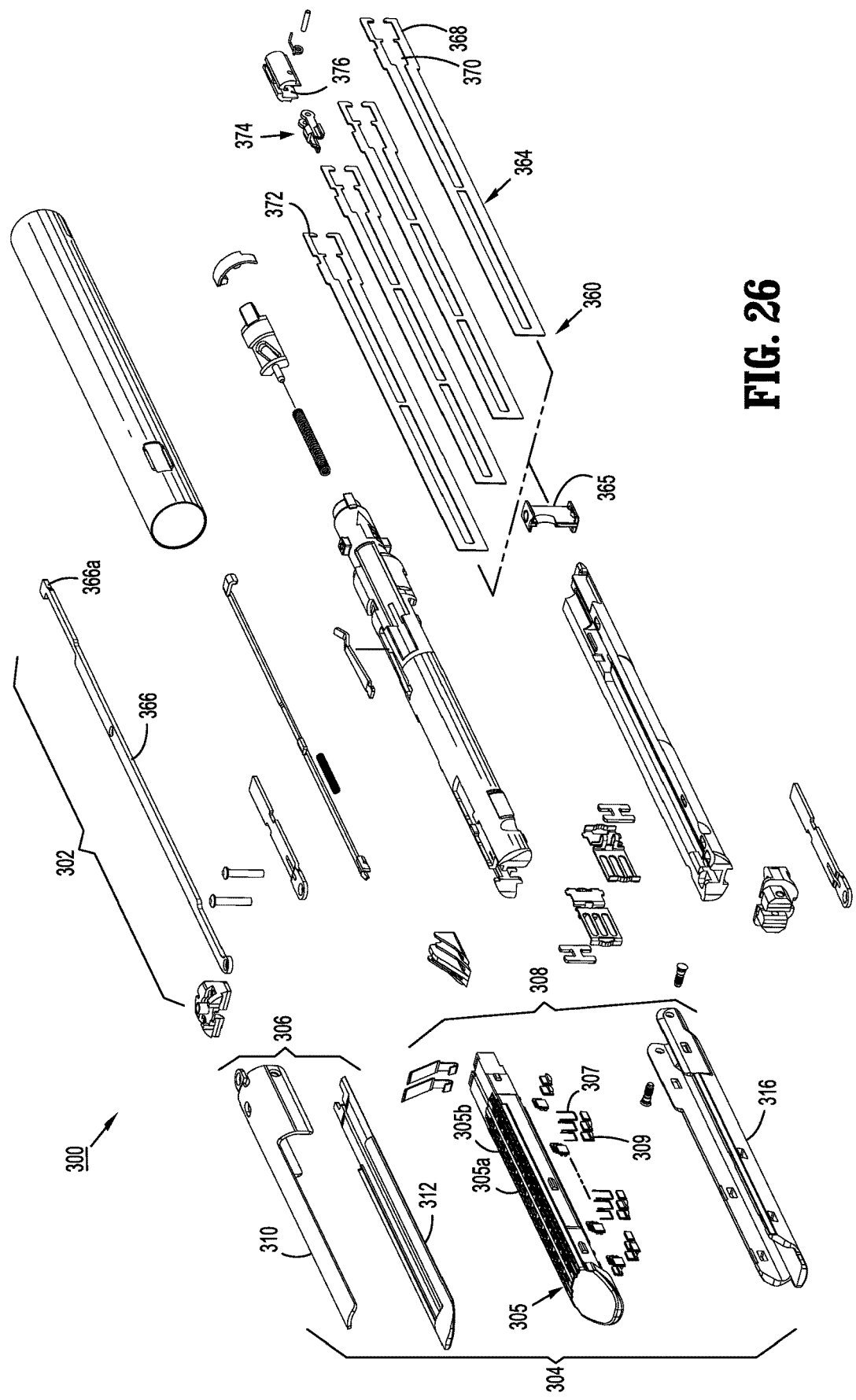
FIG. 26 is a perspective view, with parts separated, of an exemplary end effector for use with the surgical device and the adapter of the present disclosure.

Adapter 200 is configured to convert a rotation of either of drive connectors 120 and 122 of surgical device 100 into axial translation useful for operating a drive assembly 360 and an articulation link 366 of end effector 300, as illustrated in FIG. 26 and as will be discussed in greater detail below.

Adapter 200 includes a first drive transmitting/converting assembly for interconnecting third rotatable drive connector 122 of surgical device 100 and a first axially translatable drive member 360 of end effector 300, wherein the first drive transmitting/converting assembly converts and transmits a rotation of third rotatable drive connector 122 of surgical device 100 to an axial translation of the first axially translatable drive assembly 360 of end effector 300 for firing.

Adapter 200 includes a second drive transmitting/converting assembly for interconnecting second rotatable drive connector 120 of surgical device 100 and a second axially translatable drive member 366 of end effector 300, wherein the second drive transmitting/converting assembly converts and transmits a rotation of second rotatable drive connector 120 of surgical device 100 to an axial translation of articulation link 366 of end effector 300 for articulation.

Figure 10:
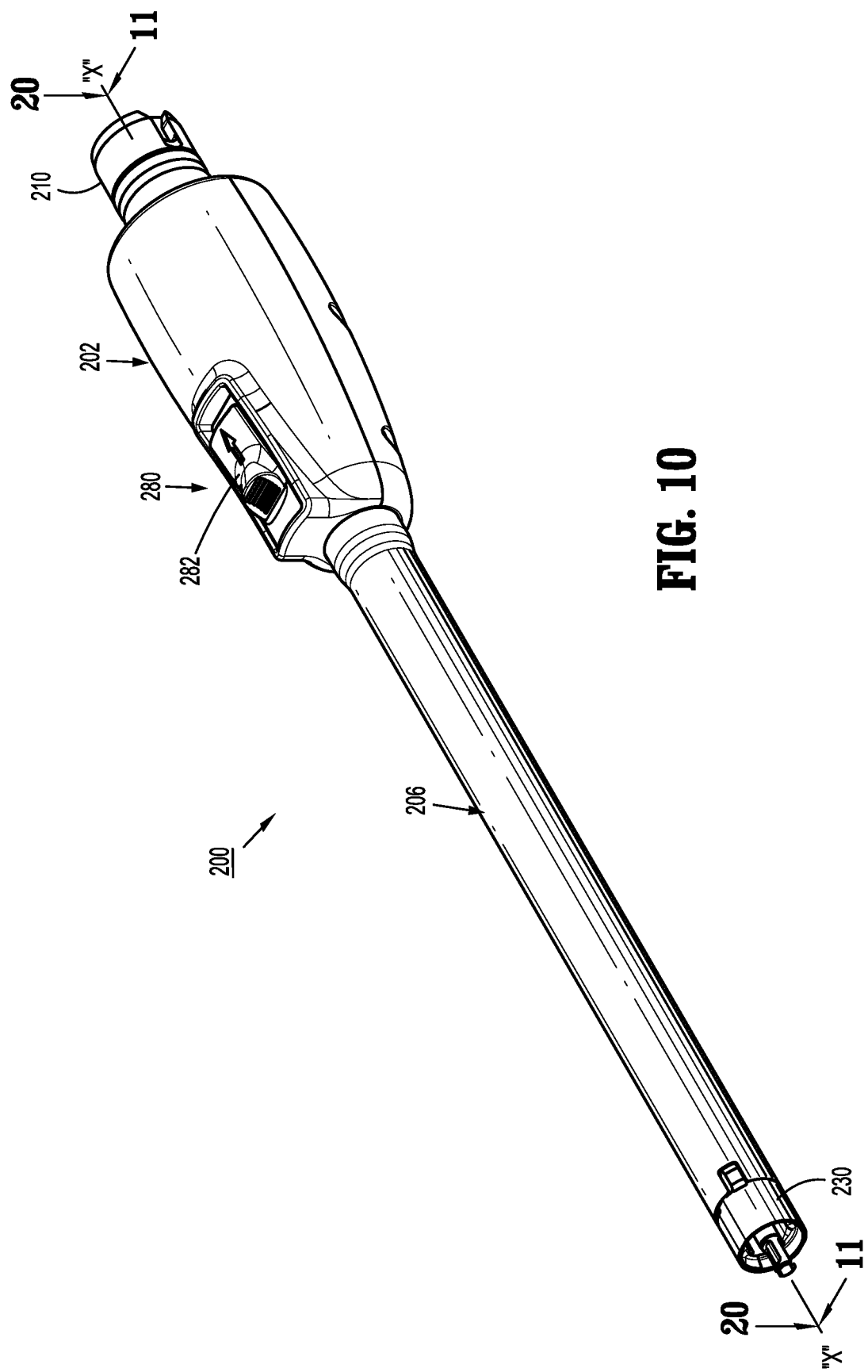
FIG. 10 is a perspective view of the adapter of FIG. 1.

Turning now to FIG. 10, adapter 200 includes a knob housing 202 and an outer tube 206 extending from a distal end of knob housing 202. Knob housing 202 and outer tube 206 are configured and dimensioned to house the components of adapter 200. Outer tube 206 is dimensioned for endoscopic insertion, in particular, that outer tube is passable through a typical trocar port, cannula or the like. Knob housing 202 is dimensioned to not enter the trocar port, cannula of the like.

Knob housing 202 is configured and adapted to connect to connecting portion 108*a* of upper housing portion 108 of distal half-section 110*a* of surgical device 100.

Figure 11:
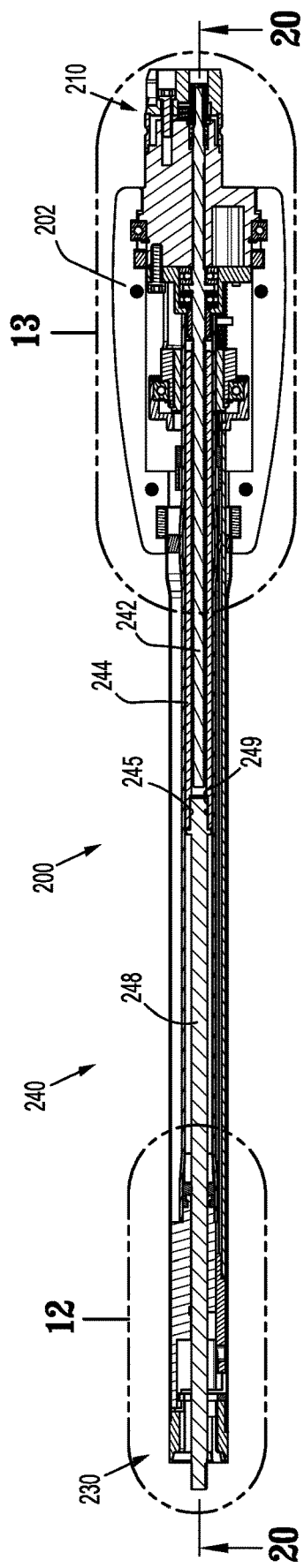
FIG. 11 is a cross-sectional view of the adapter of FIGS. 1 and 10, as taken through 11-11 of FIG. 10.
Figure 14:
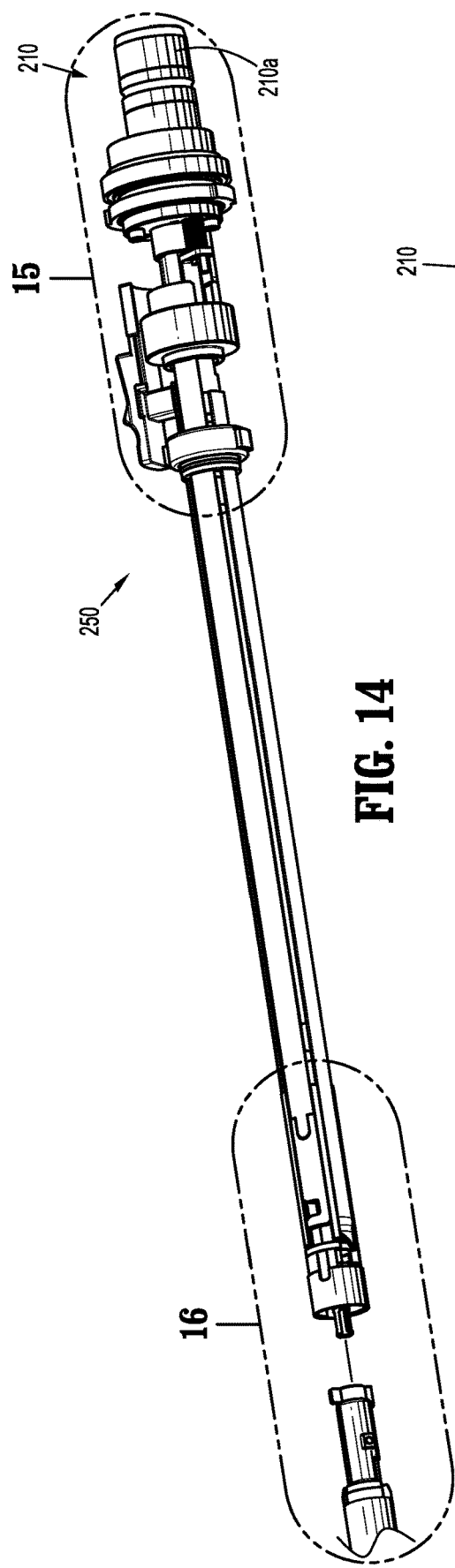
FIG. 14 is a perspective view, with some parts omitted, of the adapter and a portion of a loading unit.
Figure 15:
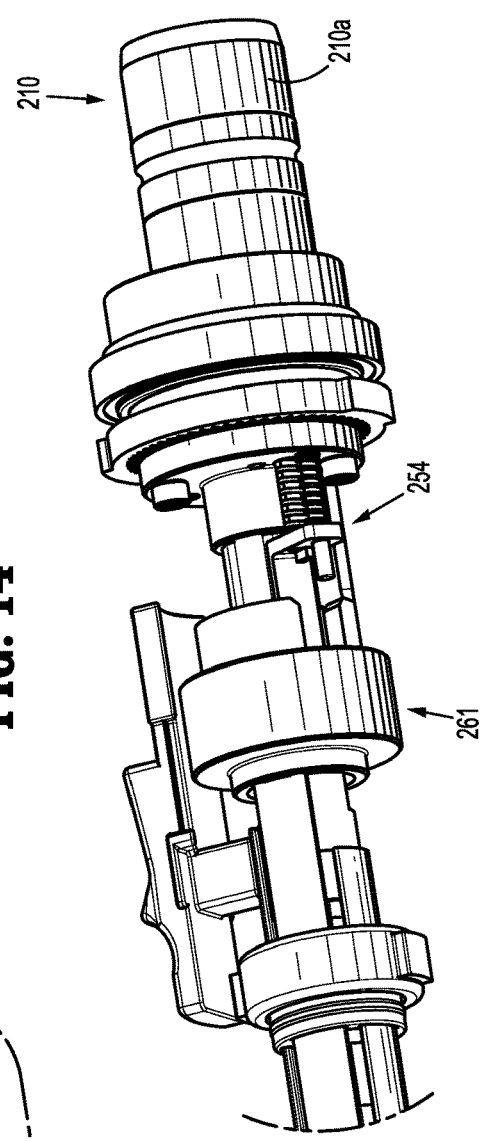
FIG. 15 is an enlarged view of the indicated area of detail of FIG. 14.

As seen in FIGS. 10, 11 and 14 adapter 200 includes a surgical device drive coupling assembly 210 at a proximal end thereof and an end effector coupling assembly 230 at a distal end thereof. Drive coupling assembly 210 includes a drive coupling housing 210*a* rotatably supported, at least partially, in knob housing 202. Drive coupling assembly 210 rotatably supports a first rotatable proximal drive shaft or element 212, a second rotatable proximal drive shaft or element 214, and a third rotatable proximal drive shaft or element 216 therein (see FIG. 15, for example).

As seen in FIG. 19, drive coupling housing 210*a* is configured to rotatably support first, second and third connector sleeves 218, 220 and 222, respectively. Each of connector sleeves 218, 220, 222 is configured to mate with respective first, second and third drive connectors 118, 120, 122 of surgical device 100, as described above. Each of connector sleeves 218, 220, 222 is further configured to mate with a proximal end of respective first, second and third proximal drive shafts or elements 212, 214, 216.

Figure 22:
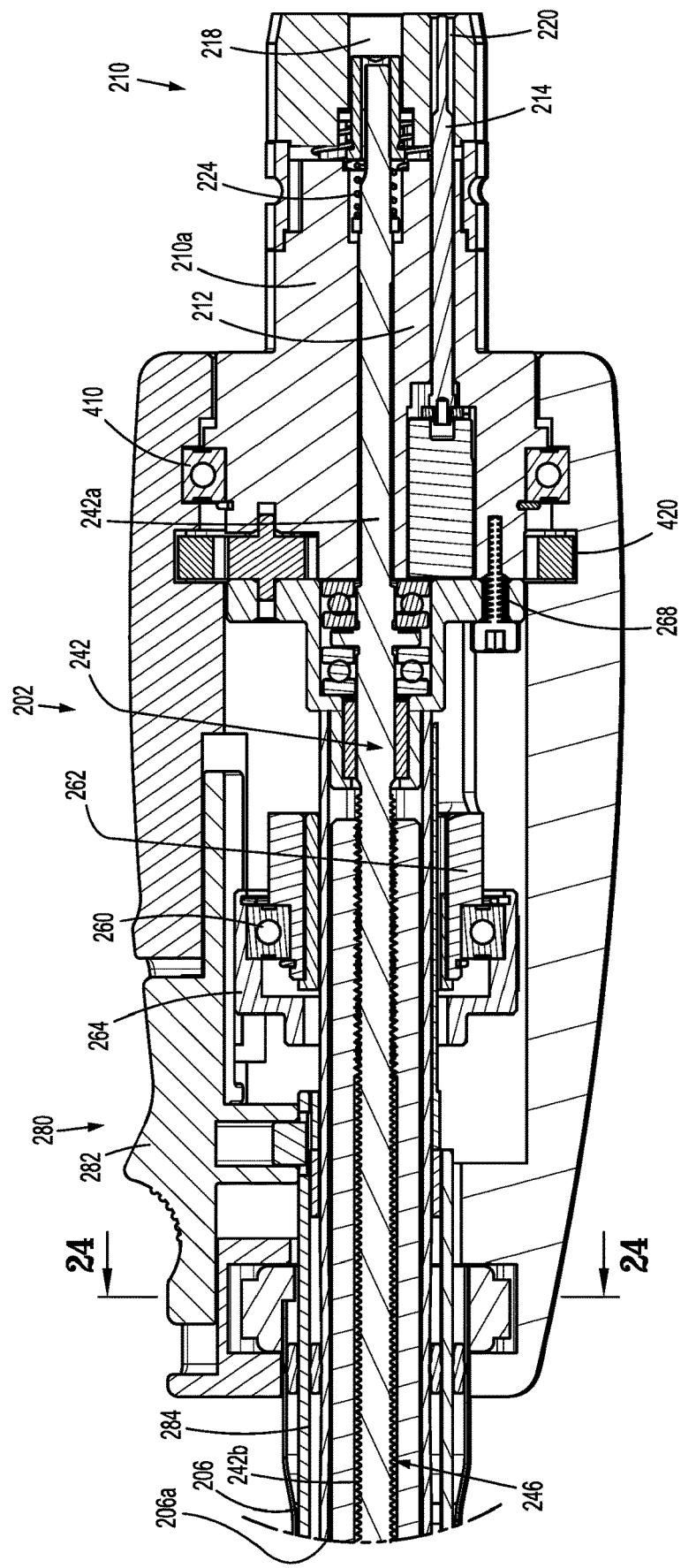
FIG. 22 is an enlarged view of the indicated area of detail of FIG. 20.
Figure 25:
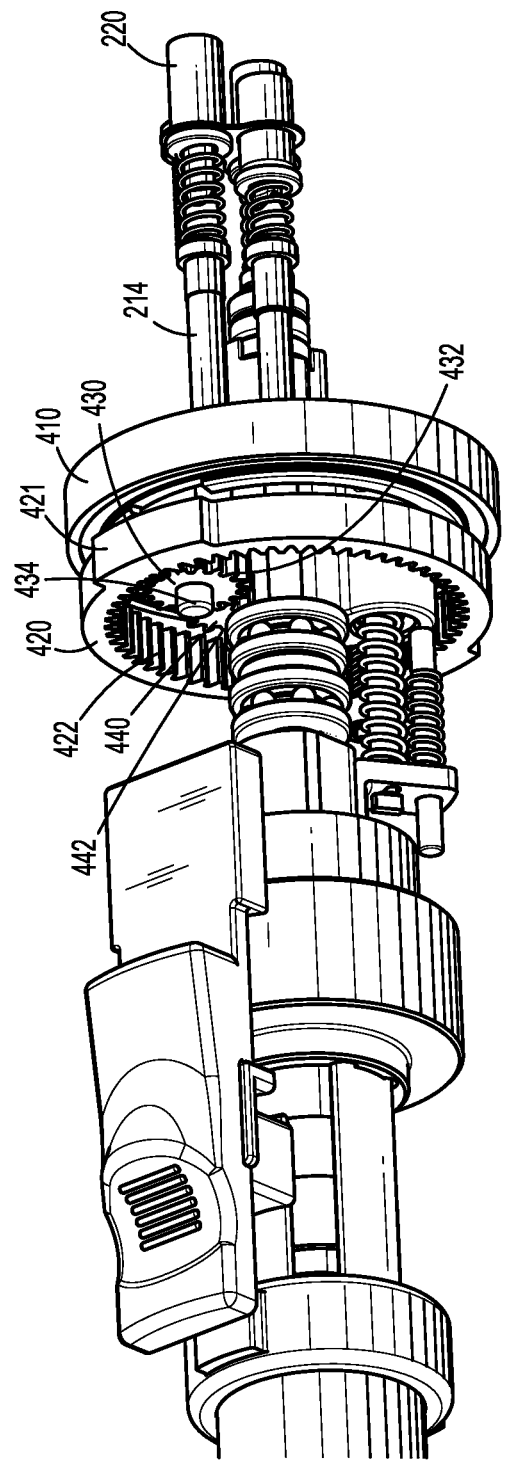
FIG. 25 is a perspective view of a portion of the adapter with parts omitted.

With particular reference to FIGS. 19 and 22, proximal drive coupling assembly 210 includes a first, a second and a third biasing member 224, 226 and 228 disposed distally of respective first, second and third connector sleeves 218, 220, 222. Each of biasing members 224, 226 and 228 is disposed about respective first, second and third rotatable proximal drive shaft 212, 214 and 216. Biasing members 224, 226 and 228 act on respective connector sleeves 218, 220 and 222 to help maintain connector sleeves 218, 220 and 222 engaged with the distal end of respective drive rotatable drive connectors 118, 120, 122 of surgical device 100 when adapter 200 is connected to surgical device 100.

In particular, first, second and third biasing members 224, 226 and 228 function to bias respective connector sleeves 218, 220 and 222 in a proximal direction. In this manner, during assembly of adapter 200 to surgical device 100, if first, second and/or third connector sleeves 218, 220 and/or 222 is/are misaligned with the drive connectors 118, 120, 122 of surgical device 100, first, second and/or third biasing member(s) 224, 226 and/or 228 are compressed. Thus, when drive mechanism 160 of surgical device 100 is engaged, drive connectors 118, 120, 122 of surgical device 100 will rotate and first, second and/or third biasing member(s) 224, 226 and/or 228 will cause respective first, second and/or third connector sleeve(s) 218, 220 and/or 222 to slide back proximally, effectively coupling drive connectors 118, 120, 122 of surgical device 100 to first, second and/or third proximal drive shaft(s) 212, 214 and 216 of proximal drive coupling assembly 210.

Upon calibration of surgical device 100, each of drive connectors 118, 120, 122 of surgical device 100 is rotated and the bias on connector sleeve(s) 218, 220 and 222 properly seats connector sleeve(s) 218, 220 and 222 over the respective drive connectors 118, 120, 122 of surgical device 100 when the proper alignment is reached.

Figure 20:
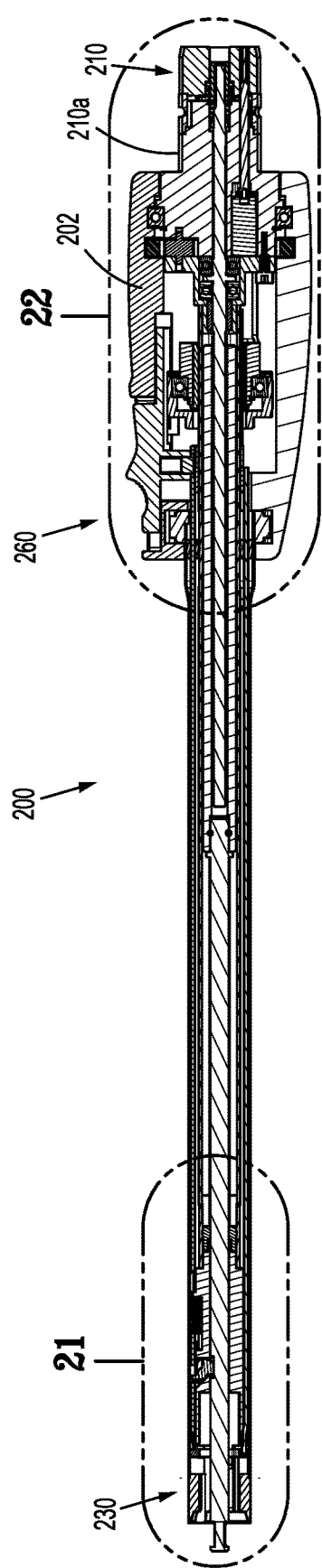
FIG. 20. is a cross-sectional view of the adapter of FIGS. 1 and 10, as taken through 20-20 of FIG. 10.

Adapter 200, as seen in FIGS. 11, 14 and 20, includes a first, a second and a third drive transmitting/converting assembly 240, 250, 260, respectively, disposed within handle housing 202 and outer tube 206. Each drive transmitting/converting assembly 240, 250, 260 is configured and adapted to transmit or convert a rotation of a first, second and third drive connector 118, 120, 122 of surgical device 100 into axial translation of a distal drive member 248 and drive bar (or articulation bar) 258 of adapter 200, to effectuate closing, opening, articulating and firing of end effector 300; or a rotation of ring gear 266 of adapter 200, to effectuate rotation of handle housing 202 of adapter 200.

Figure 12:
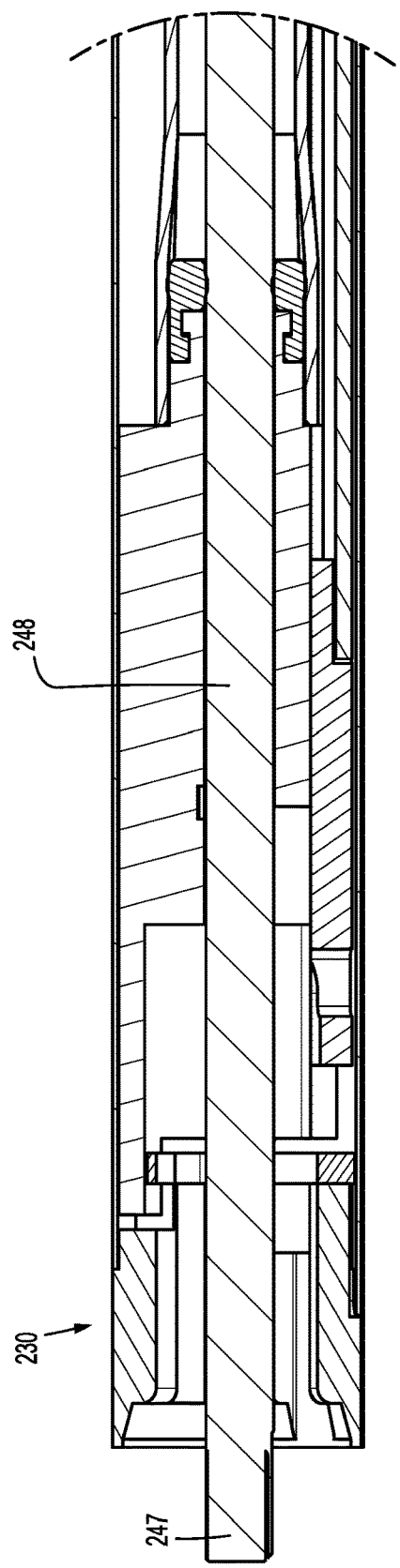
FIG. 12 is an enlarged view of the indicated area of detail of FIG. 11.
Figure 13:
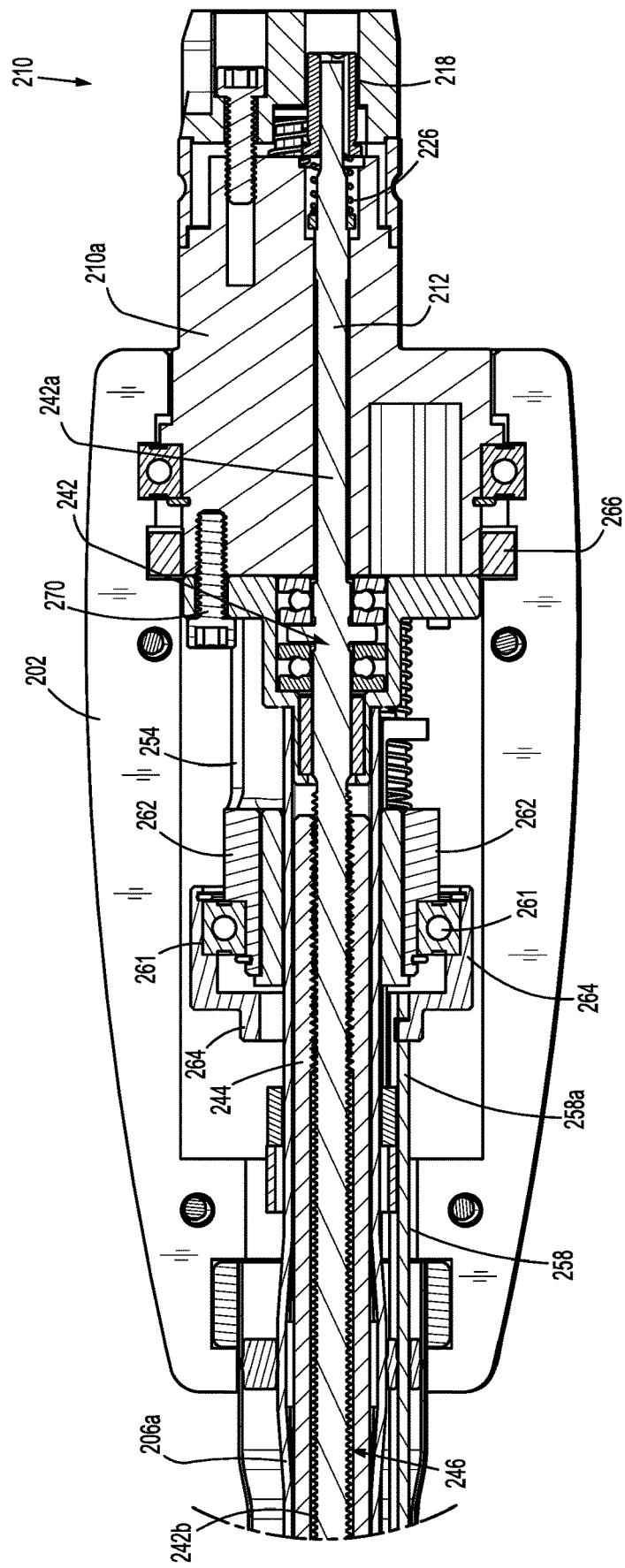
FIG. 13 is an enlarged view of the indicated area of detail of FIG. 11.

As seen in FIGS. 11-13, first drive transmitting/converting assembly 240 includes a first distal drive shaft 242 rotatably supported within housing 202 and outer tube 206.

A proximal end portion 242a of first distal drive shaft 242 extends distally from first proximal drive shaft 212. First distal drive shaft 242 further includes a threaded portion 242b having a threaded outer profile or surface.

First drive transmitting/converting assembly 240 further includes a drive coupling nut 244 rotatably coupled to threaded distal end portion 242b of first distal drive shaft 242, and which is slidably disposed within outer tube 206. Drive coupling nut 244 is keyed to an inner housing tube 206a of outer tube 206 so as to be prevented from rotation as first distal drive shaft 242 is rotated. In this manner, as first distal drive shaft 242 is rotated, drive coupling nut 244 is translated longitudinally through and/or along inner housing tube 206a of outer tube 206.

First drive transmitting/converting assembly 240 further includes a distal drive member 248 that is mechanically engaged with drive coupling nut 244, such that axial movement of drive coupling nut 244 results in a corresponding amount of axial movement of distal drive member 248. More particularly, distal end of coupling nut 244 includes at least one inwardly depending projection 245 that engages at least one corresponding groove 249 disposed on a proximal portion of the distal drive member 248 (see FIG. 11). The distal end portion of distal drive member 248 supports a connection member 247 configured and dimensioned for selective engagement with drive member 374 of drive assembly 360 of end effector 300.

In operation, as first rotatable proximal drive shaft 212 is rotated, due to a rotation of first connector sleeve 218, as a result of the rotation of the first respective drive connector 118 of surgical device 100, first distal drive shaft 242 rotates. As first distal drive shaft 242 is rotated, drive coupling nut 244 is caused to be translated axially along first distal drive shaft 242. As drive coupling nut 244 is caused to be translated axially along first distal drive shaft 242, distal drive member 248 is caused to be translated axially relative to inner housing tube 206a of outer tube 206. As distal drive member 248 is translated axially, with connection member 247 connected thereto and engaged with drive member 374 of drive assembly 360 of end effector 300, distal drive member 248 causes concomitant axial translation of drive member 374 of end effector 300 to effectuate a closure of tool assembly 304 and a firing of tool assembly 304 of end effector 300.

With reference to FIGS. 13-22, second drive converter assembly 250 of adapter 200 includes second rotatable proximal drive shaft 216 rotatably supported within drive coupling assembly 210. Second rotatable proximal drive shaft 216 includes a non-circular or shaped proximal end portion configured for connection with second connector or coupler 222 which is connected to respective second connector 120 of surgical device 100. Second rotatable proximal drive shaft 216 further includes a distal end portion 216b having a threaded outer profile or surface.

Distal end portion 216b of proximal drive shaft 216 is threadably engaged with a nut 252. Nut 252 is disposed in mechanical cooperation with a proximal portion 254a of an articulation sleeve 254. For example, nut 252 extends through a recess 255 within articulation sleeve 254. A distal portion 254b of articulation sleeve 254 is disposed in mechanical cooperation (e.g., attached or coupled to) with an articulation bearing 261, and in particular with an inner sleeve 262 of articulation bearing 261. An outer sleeve 264 of articulation bearing 261 is mechanically coupled to a proximal portion 258a of articulation bar 258. A distal portion 258b of articulation bar 258 includes a slot 272 therein, which is configured to accept a portion (e.g., a flag, articulation link 366, etc.) of loading unit 300. Further, slot 272 includes a tapered entry section 274, which is configured to reduce the clearance between loading unit 300 and articulation bar 258, thus facilitating alignment and/or engagement therebetween.

With further regard to articulation bearing 261, articulation bearing 261 is both rotatable and longitudinally translatable. Additionally, it is envisioned that articulation bearing 261 allows for free, unimpeded rotational movement of loading unit 300 when its jaw members 306, 308 are in an approximated position and/or when jaw members 306, 308 are articulated. Further, articulation bearing 261 reduces the amount of friction that is typically associated with rotation of articulated and/or approximated jaw members, as articulated and/or approximated jaw members generally generate significant loads on the rotational and/or articulation systems.

In operation, as drive shaft 216 is rotated due to a rotation of second connector sleeve 222, as a result of the rotation of the second drive connector 120 of surgical device 100, nut 252 is caused to be translated axially along threaded distal end portion 216b of proximal drive shaft 216, which in turn causes articulation sleeve 254 to be axially translated relative to knob housing 202. As articulation sleeve 254 is translated axially, articulation bearing 261 is caused to be translated axially. Accordingly, as articulation bearing 261 is translated axially, articulation bar 258 is caused to axially translate, which causes concomitant axial translation of an articulation link 366 of end effector 300 to effectuate an articulation of tool assembly 304.

As seen in FIGS. 20-25 and as mentioned above, adapter 200 includes a third drive transmitting/converting assembly 260 supported in knob housing 202. Third drive transmitting/converting assembly 260 includes a tube assembly 400, a rotation bearing 410, a rotation ring gear 420, an idler gear 430 and a spur gear 440. Tube assembly 400 includes a housing tip 402, a tube 206 and a tube coupler 406. Housing tip 402 is distally disposed adjacent connection member 247. Tube coupler 406 is disposed adjacent a proximal end of tube assembly 400. Tube 206 extends between housing tip 402 and tube coupler 406. As shown in FIG. 24, tube coupler 406 is mechanically coupled adjacent distal ends of upper and lower portions handle or knob housing 202. The proximal portion of knob housing 202 is positioned around rotation bearing 410, which allows rotation therebetween.

With further regard to rotation bearing 410, rotation bearing 410 is non-rotatable with respect to drive coupling housing 210a, and is both rotatable and longitudinally translatable with respect to knob housing 202. Additionally, it is envisioned that rotation bearing 410 allows for free, unimpeded rotational movement of loading unit 300 when its jaw members 306, 308 are in an approximated position and/or when jaw members are articulated. Further, rotation bearing 410 reduces the amount of friction that is typically associated with rotation of articulated and/or approximated jaw members, as articulated and/or approximated jaw members generally generate significant loads on the rotational and/or articulation systems.

Rotation ring gear 420 is disposed distally of rotation bearing 410 and is non-rotatable with respect to knob housing 202 (e.g., due to protrusions 421 of ring gear 420 being captured by corresponding recesses in knob housing 202). Rotation ring gear 420 includes a plurality of teeth 422 disposed around an inner circumference thereof. Idler gear 430 is rotatable about a pin 434, and includes a plurality of teeth 432 disposed around an outer circumference thereof, which are configured and positioned to engage teeth 422 of rotation ring gear 420. Spur gear 440 includes a plurality of teeth 442 disposed around an outer circumference thereof, which are configured and positioned to engage teeth 432 of idler gear 430. Additionally, spur gear 440 is attached to second rotatable proximal drive shaft 214.

In operation, rotation of second drive connector 120 of surgical device 100 causes second connector sleeve 220 and drive shaft 214 to rotate. Rotation of drive shaft 214 causes spur gear 440 to rotate. Rotation of spur gear 440 results in rotation of idler gear 430, which causes ring gear 420 to likewise rotate. Since ring gear 420 is non-rotatable with respect to knob housing 202, rotation of ring gear 420 causes knob housing 202 to rotate. Further, due to the engagement between knob housing 202 and tube coupler 406, rotation of knob housing 202 causes tube coupler 406, tube 206, housing tip 402, and distal coupling assembly 230 to rotate about longitudinal axis "A-A" defined by adapter 200 (see FIG. 1). As distal coupling assembly 230 is rotated, end effector 300, that is connected to distal coupling assembly 230, is also caused to be rotated about longitudinal axis of adapter 200

Figure 21:
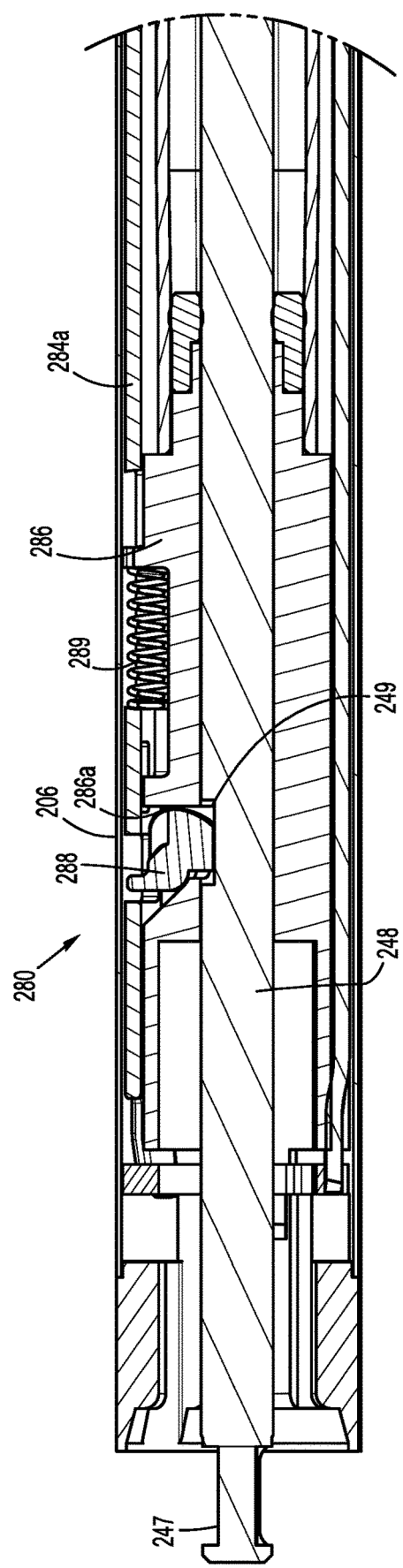
FIG. 21 is an enlarged view of the indicated area of detail of FIG. 20.

With reference to FIGS. 21 and 22, adapter 200 further includes a lock mechanism 280 for fixing the axial position and radial orientation of distal drive member 248. Lock mechanism 280 includes a button 282 slidably supported on knob housing 202. Lock button 282 is connected to an actuation bar 284 that extends longitudinally through outer tube 206. Actuation bar 284 is interposed between outer tube 206 and inner housing tube 206a. Actuation bar 284 moves upon a movement of lock button 282. Upon a predetermined amount of movement of lock button 282, a distal end 284a of actuation bar 284 moves into contact with lock out 286, which causes lock out 286 to cam a camming member 288 from a recess 249 in distal drive member 248. When camming member 288 is in engagement with recess 249 (e.g., at least partially within recess 249), the engagement between camming member 288 and distal drive member 248 effectively locks the axial and rotational position of end effector 300 that is engaged with connection member 247.

In operation, in order to lock the position and/or orientation of distal drive member 248, a user moves lock button 282 from a distal position to a proximal position, thereby causing lock out 286 to move proximally such that a distal face 286a of lock out 286 moves out of contact with camming member 288, which causes camming member 288 to cam into recess 249 of distal drive member 248. In this manner, distal drive member 248 is prevented from distal and/or proximal movement. When lock button 282 is moved from the proximal position to the distal position, distal end 284a of actuation bar 284 moves distally into lock out 286, against the bias of biasing member 289, to force camming member 288 to out of recess 249, thereby allowing unimpeded axial translation and radial movement of distal drive member 248. When drive member 248 has translated to initiate closure of tool assembly 304, lock button 282 cannot be actuated and the end effector 300 cannot be removed until tool assembly 304 is reopened.

As seen in FIG. 6 adapter 200 includes a pair of electrical contact pins 290a, 290b for electrical connection to a corresponding electrical plug 190a, 190b disposed in connecting portion 108a of surgical device 100. Electrical contacts 290a, 290b serve to allow for calibration and communication of life-cycle information to circuit board 150 of surgical device 100 via electrical plugs 190a, 190b that are electrically connected to circuit board 150. Adapter 200 further includes a circuit board supported in knob housing 202 and which is in electrical communication with electrical contact pins 290a, 290b.

When a button of surgical device is activated by the user, the software checks predefined conditions. If conditions are met, the software controls the motors and delivers mechanical drive to the attached surgical stapler, which can then open, close, rotate, articulate or fire depending on the function of the pressed button. The software also provides feedback to the user by turning colored lights on or off in a defined manner to indicate the status of surgical device 100, adapter 200 and/or end effector 300.

A high level electrical architectural view of the system is displayed below in Schematic "A" and shows the connections to the various hardware and software interfaces. Inputs from presses of buttons 124, 126 and from motor encoders of the drive shaft are shown on the left side of Schematic "A". The microcontroller contains the device software that operates surgical device 100, adapter 200 and/or end effector 300. The microcontroller receives inputs from and sends outputs to a MicroLAN, an Ultra ID chip, a Battery ID chip, and Adaptor ID chips. The MicroLAN, the Ultra ID chip, the Battery ID chip, and the Adaptor ID chips control surgical device 100, adapter 200 and/or end effector 300 as follows:

MicroLAN—Serial 1-wire bus communication to read/write system component ID information.

Ultra ID chip—identifies surgical device 100 and records usage information.

Battery ID chip—identifies the Battery 156 and records usage information.

Adaptor ID chip—identifies the type of adapter 200, records the presence of an end effector 300, and records usage information.

Figure 27:
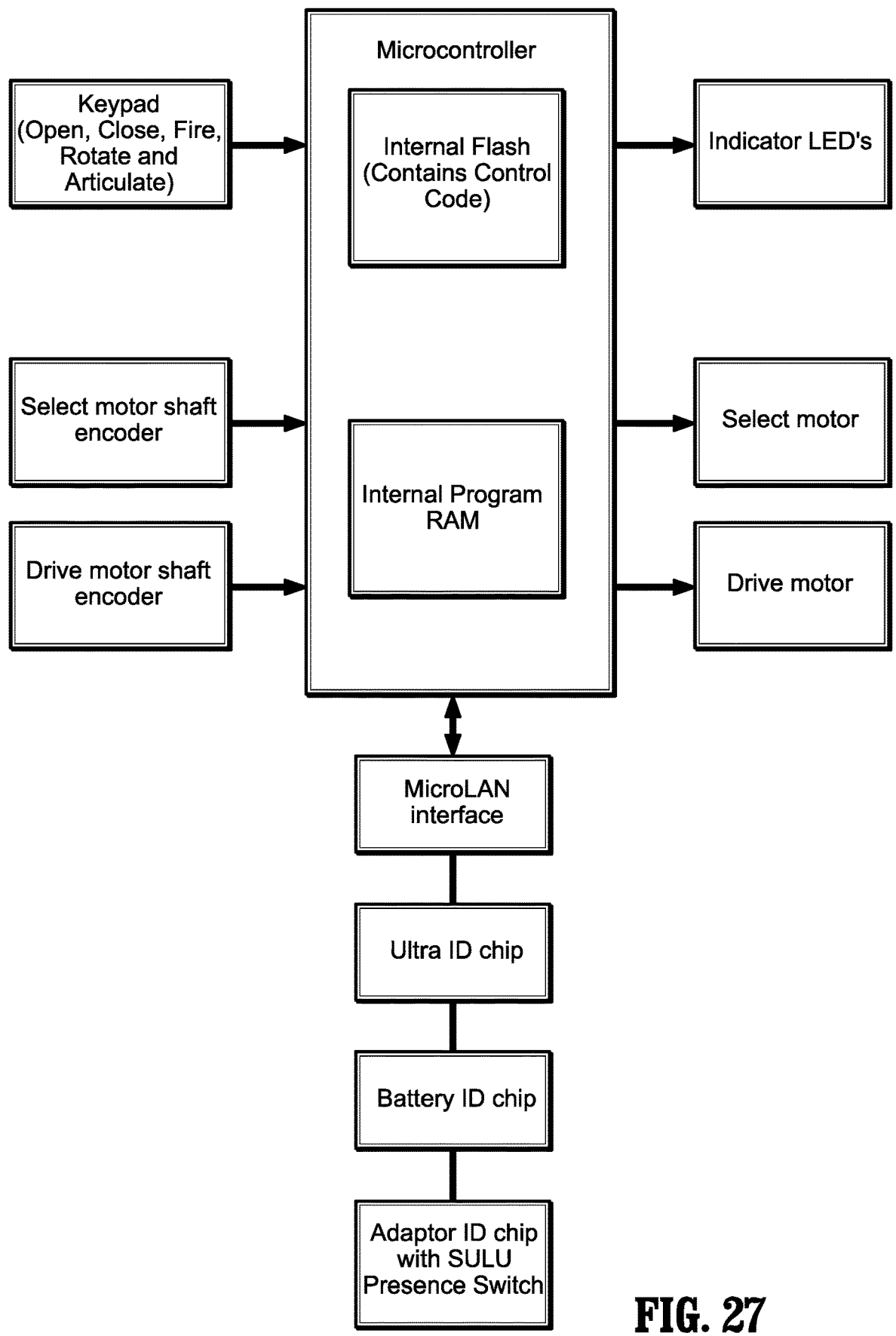
FIG. 27 is a schematic illustration of the outputs to the LEDs; selection of motor (to select clamping/cutting, rotation or articulation); and selection of the drive motors to perform a function selected.

The right side of the schematic illustrated in FIG. 27 indicates outputs to the LEDs; selection of motor (to select clamping/cutting, rotation or articulation); and selection of the drive motors to perform the function selected.

As illustrated in FIGS. 1 and 26, the end effector is designated as 300. End effector 300 is configured and dimensioned for endoscopic insertion through a cannula, trocar or the like. In particular, in the embodiment illustrated in FIGS. 1 and 26, end effector 300 may pass through a cannula or trocar when end effector 300 is in a closed condition.

End effector 300 includes a proximal body portion 302 and a tool assembly 304. Proximal body portion 302 is releasably attached to a distal coupling 230 of adapter 200 and tool assembly 304 is pivotally attached to a distal end of proximal body portion 302. Tool assembly 304 includes an anvil assembly 306 and a cartridge assembly 308. Cartridge assembly 308 is pivotal in relation to anvil assembly 306 and is movable between an open or unclamped position and a closed or clamped position for insertion through a cannula of a trocar.

Proximal body portion 302 includes at least a drive assembly 360 and an articulation link 366.

Referring to FIG. 26, drive assembly 360 includes a flexible drive beam 364 having a distal end which is secured to a dynamic clamping member 365, and a proximal engagement section 368. Engagement section 368 includes a stepped portion defining a shoulder 370. A proximal end of engagement section 368 includes diametrically opposed inwardly extending fingers 372. Fingers 372 engage a hollow drive member 374 to fixedly secure drive member 374 to the proximal end of beam 364. Drive member 374 defines a proximal porthole 376 which receives connection member 247 of drive tube 246 of first drive converter assembly 240 of adapter 200 when end effector 300 is attached to distal coupling 230 of adapter 200.

When drive assembly 360 is advanced distally within tool assembly 304, an upper beam of clamping member 365 moves within a channel defined between anvil plate 312 and anvil cover 310 and a lower beam moves over the exterior surface of carrier 316 to close tool assembly 304 and fire staples therefrom.

Proximal body portion 302 of end effector 300 includes an articulation link 366 having a hooked proximal end 366a which extends from a proximal end of end effector 300. Hooked proximal end 366a of articulation link 366 engages coupling hook 258c of drive bar 258 of adapter 200 when end effector 300 is secured to distal housing 232 of adapter 200. When drive bar 258 of adapter 200 is advanced or retracted as described above, articulation link 366 of end effector 300 is advanced or retracted within end effector 300 to pivot tool assembly 304 in relation to a distal end of proximal body portion 302.

As illustrated in FIG. 26, cartridge assembly 308 of tool assembly 304 includes a staple cartridge 305 supportable in carrier 316. Staple cartridge 305 defines a central longitudinal slot 305a, and three linear rows of staple retention slots 305b positioned on each side of longitudinal slot 305a. Each of staple retention slots 305b receives a single staple 307 and a portion of a staple pusher 309. During operation of surgical device 100, drive assembly 360 abuts an actuation sled and pushes actuation sled through cartridge 305. As the actuation sled moves through cartridge 305, cam wedges of the actuation sled sequentially engage staple pushers 309 to move staple pushers 309 vertically within staple retention slots 305b and sequentially eject a single staple 307 therefrom for formation against anvil plate 312.

Reference may be made to U.S. Patent Publication No. 2009/0314821, filed on Aug. 31, 2009, entitled "TOOL ASSEMBLY FOR A SURGICAL STAPLING DEVICE" for a detailed discussion of the construction and operation of end effector 300.

It will be understood that various modifications may be made to the embodiments of the presently disclosed adapter assemblies. For example, the battery 156 may be replaced with alternate sources of electrical power such as line voltage (either AC or DC) or a fuel cell. Therefore, the above description should not be construed as limiting, but merely as exemplifications of embodiments. Those skilled in the art will envision other modifications within the scope and spirit of the present disclosure.

What is claimed is:

1. An adapter assembly comprising:
    an outer tube housing defining a longitudinal axis and configured to releasably couple to a handle assembly;
    a drive shaft rotatably supported in the outer tube housing and parallel to the longitudinal axis, the drive shaft having a distal portion and a proximal portion configured to engage a drive connector of the handle assembly;
    a nut connected to the distal portion of the drive shaft such that rotation of the drive shaft translates the nut in a direction parallel to the longitudinal axis;
    a distal drive member having a distal portion configured to engage a drive link of a loading unit and a proximal portion coupled to the nut and configured to translate in response to translation of the nut; and
    a lock mechanism configured to secure axial position and radial orientation of the distal drive member.

2. The adapter assembly according to claim 1, wherein the nut is threadably coupled to the distal portion of the drive shaft.

3. The adapter assembly according to claim 1, wherein the distal drive member includes a recess and the lock mechanism includes a camming member configured to engage the recess.

4. The adapter assembly according to claim 3, further comprising a knob housing coupled to a proximal end of the outer tube housing.

5. The adapter assembly according to claim 4, wherein the lock mechanism further includes a button slidably supported on the knob housing.

6. The adapter assembly according to claim 5, wherein the lock mechanism further includes an actuation bar extending through the outer tube housing.

7. The adapter assembly according to claim 6, wherein the actuation bar is mechanically engaged to the button such that the actuation bar is movable in response to movement of the button.

8. The adapter assembly according to claim 7, wherein the lock mechanism further includes a lockout configured to engage the camming member and mechanically engaged to the actuation bar.

9. The adapter assembly according to claim 8, wherein the actuation bar is configured to move the camming member to engage or disengage the recess.

10. The adapter assembly according to claim 9, wherein movement of the actuation bar to a locked configuration causes the lockout to disengage the camming member and the camming member to engages the recess thereby preventing longitudinal movement of the distal drive member.

11. The adapter assembly according to claim 10, wherein movement of the actuation bar to an unlocked configuration causes the lockout to engage the camming member and the camming member to disengage the recess thereby allowing for longitudinal movement of the distal drive member.

12. The adapter assembly according to claim 11, wherein the actuation bar is movable in a proximal direction into the locked configuration and is movable in a distal direction into the unlocked configuration.

* * * * *